(12) United States Patent
Mitsui et al.

(10) Patent No.: US 6,380,435 B2
(45) Date of Patent: Apr. 30, 2002

(54) PURIFYING PROCESS OF TETRAKIS (FLUOROARYL)BORATE.MAGNESIUM HALIDE, TETRAKIS(FLUOROARYL) BORATE·ETHER COMPLEX AND PRODUCING PROCESS OF THE SAME, AND PRODUCING PROCESS OF TETRAKIS (FLUOROARYL)BORATE DERIVATIVE

(75) Inventors: Hitoshi Mitsui, Nara; Tsunemasa Ueno, Ikeda; Ikuyo Ikeno, Osaka; Naoko Yamamoto, Nishinomiya, all of (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/779,673

(22) Filed: Feb. 9, 2001

Related U.S. Application Data

(62) Division of application No. 09/171,832, filed as application No. PCT/JP98/00946 on Mar. 9, 1998, now Pat. No. 6,215,025.

(30) Foreign Application Priority Data

| Mar. 10, 1997 | (JP) | 9-55310 |
| Mar. 10, 1997 | (JP) | 9-55311 |
| Mar. 10, 1997 | (JP) | 9-55312 |

(51) Int. Cl.$^7$ .................................................. C07F 5/02
(52) U.S. Cl. .................................................. 568/6; 568/1
(58) Field of Search ............................... 568/1, 6

(56) References Cited

U.S. PATENT DOCUMENTS

| 3,055,943 A | * | 9/1962 | Honeycutt |
| 3,078,308 A | * | 2/1963 | Brown |
| 4,224,256 A | | 9/1980 | Klemann et al. |
| 5,473,036 A | | 12/1995 | Piotrowski et al. |

FOREIGN PATENT DOCUMENTS

| DE | EP0662478 A1 | 7/1995 |
| EP | 0604963 | 7/1994 |
| EP | 0609452 | 8/1994 |
| GB | 705719 | 3/1954 |
| JP | 63238087 | 10/1988 |
| JP | 9400459 | 1/1994 |
| JP | 6247980 | 9/1994 |
| JP | 6247981 | 9/1994 |
| JP | 7267966 | 10/1995 |

OTHER PUBLICATIONS

CA:123:229277 abs of WO 9503338 Feb. 1995.*
CA:128:13514 abs of WO 9742231 Nov. 1997.*
CA:127:51114 abs of WO 9717380 May 1997.*
J. Oranometal. Chem.2 (1964) pp. 245–250.
Vandenberg, John T. et al., "Part III. The Preparation and Reagent Properties of Sodium Tetrakis(p–Trifluoromethylphenyl)Borate and Sodum Tetrakis (m–Fluorophenyl)Borate", Analytica Chimica Acta, vol. 44, 1969, pp. 175–183.
Jia, Li et al., "Protected (Fluoroaryl) Borates as Effective Counteranions for Cationic Metallocene Polymerization Catalysts", Organometallics, vol. 14, 1995, pp. 3135–3137.

* cited by examiner

Primary Examiner—Jean E. Vollano
(74) Attorney, Agent, or Firm—Birch, Stewart, Kolasch & Birch, LLP

(57) ABSTRACT

Tetrakis (fluoroaryl)borate.magnesium halide ($Ar_4BMgX$) expressed by General Formula (1):

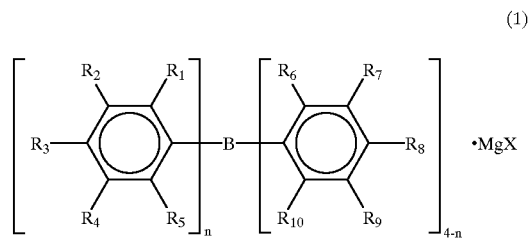

(1)

where each of $R_1$–$R_{10}$ represents a hydrogen atom, a fluorine atom, a hydrocarbon group, or an alkoxy group, provided that at least one of $R_1$–$R_5$ represents a fluorine atom and at least one of $R_6$–$R_{10}$ represents a fluorine atom, X represents a chlorine atom, a bromine atom, or an iodide atom, and n represents 2 or 3, is treated with alkali metal salts of carboxylic acid and/or alkali earth metal salts of carboxylic acid. Then, a tetrakis(fluoroaryl)borate derivative ($Ar_4BZ$) is produced by reacting treated $Ar_4BMgX$ with a compound generating monovalent cation seeds (for example, N,N-dimethylaniline.hydrochloride). Consequently, it has become possible to provide a purifying process of separating/removing impurities from $Ar_4BMgX$ readily and efficiently, and a process of producing inexpensive $Ar_4BX$ efficiently.

12 Claims, No Drawings

US 6,380,435 B2

PURIFYING PROCESS OF TETRAKIS (FLUOROARYL)BORATE.MAGNESIUM HALIDE, TETRAKIS(FLUOROARYL) BORATE·ETHER COMPLEX AND PRODUCING PROCESS OF THE SAME, AND PRODUCING PROCESS OF TETRAKIS (FLUOROARYL)BORATE DERIVATIVE

This application is a divisional application of U.S. application Ser. No. 09/171,832 filed on Oct. 26, 1998, now U.S. Pat. No. 6,215,025, which is the national phase under 35 U.S.C. §371 of prior PCT International Application No. PCT/JP98/00946 which has an International filing date of Mar. 9, 1998 which designated the United States of America, the entire contents of which are hereby incorporated by reference.

TECHNICAL FIELD

The present invention relates to ① a purifying process of tetrakis(fluoroaryl)borate.magnesium halide. The present invention also relates to ② a tetrakis(fluoroaryl)borate.ether complex, which is useful as, for example, a co-catalyst of a metallocene catalyst (polymeric catalyst) used in a cationic complex polymerization reaction, a photopolymeric catalyst for silicone, a cationic polymerization initiator used in the polymerization of a functional polymer or monomer with photochemical activation or irradiation of electron beams, and an intermediate for producing tetrakis (pentafluorophenyl)borate derivatives of various kinds, and to a process of producing the same; and to ③ a process of producing a tetrakis(fluoroaryl)borate derivative. Further, the present invention relates to ④ a tetrakis(fluoroaryl) borate derivative.ether complex useful as an intermediate for producing the tetrakis(fluoroaryl)borate derivative and a process of producing the same, and to ⑤ a process of producing tetrakis(fluoroaryl)borate.

TECHNICAL BACKGROUND

A tetrakis (fluoroaryl) borate derivative is an useful compound as, for example, a co-catalyst for promoting the activity of a metallocene catalyst (polymeric catalyst) used in a cationic complex polymerization reaction, or a photopolymeric catalyst for silicone. Also, tetrakis(fluoroaryl) borate.magnesium halide is an useful compound as an intermediate for producing the tetrakis(fluoroaryl)borate derivative. Recently, the metallocene catalyst has been receiving considerable attention as a polyolefin polymeric catalyst.

A producing process of tetrakis(pentafluorophenyl) borate.magnesium bromide, which is a kind of tetrakis (fluoroaryl)borate.magnesium halide, from bromopentafluorobenzene through the Grignard reaction is disclosed in, for example, Japanese Laid-open Patent Application No. 247980/1994 (Tokukaihei No. 6-247980).

Also, in Japanese Laid-open Patent Application No. 247981/1994 (Tokukaihei No. 6-247981), a process of synthesizing tetrakis(pentafluorophenyl)borate.lithium from pentafluorobenzene using an organic lithium compound and boron halide first, and thence reacting the resulting compound with N,N-dimethylaniline.hydrochloride is disclosed as a process of producing a tetrakis(pentafluorophenyl) borate derivative, which is a kind of the tetrakis(fluoroaryl) borate derivative.

Further, a process of producing the tetrakis (pentafluorophenyl)borate derivative by reacting tetrakis (pentafluorophenyl)borate.magnesium bromide with N,N-dimethylaniline.hydrochloride is disclosed in U.S. Pat. No. 398,236.

However, Japanese Laid-open Patent Application No. 247980/1994 (Tokukaihei No. 6-247980) neither discloses nor implies the separation/removal of magnesium halide, a by-product produced with tetrakis(pentafluorophenyl) borate.magnesium bromide, from the reaction series. If the tetrakis(pentafluorophenyl)borate derivative is produced from tetrakis(pentafluorophenyl)borate.magnesium bromide containing magnesium halide as impurities, and used as a co-catalyst of the metallocene catalyst, for example, the activity of the metallocene catalyst deteriorates considerably. The process disclosed in Japanese Laid-open Patent Application No. 247980/1994 (Tokukaihei No. 6-247980) is a producing process of tetrakis(pentafluorophenyl) borate.magnesium bromide containing magnesium halide as impurities. Thus, tetrakis(pentafluorophenyl) borate.magnesium bromide obtained through this process can not be used as an adequate intermediate for producing the tetrakis(pentafluorophenyl)borate derivative.

If typical alkali treatment is applied to tetrakis (pentafluorophenyl)borate.magnesium bromide to remove magnesium halide from tetrakis(pentaflurorphenyl) borate.magnesium bromide obtained by the process disclosed in the above publication, magnesium hydroxide is produced. Since magnesium hydroxide turns a post-treatment solution into gel, the solution can not be filtered. In other words, since magnesium halide can not be removed by the typical alkali treatment, it is difficult to separate tetrakis(pentafluorophenyl)borate.magnesium bromide obtained in the above process, or to obtain a highly-pure tetrakis(fluoroaryl)borate compound after the treatment.

Thus, there has been an increasing demand for a purifying process for separating/removing impurities, such as magnesium halide, from tetrakis(fluoroaryl)borate.magnesium halide readily and efficiently.

On the other hand, the process disclosed in Japanese Laid-open Patent Application No. 247981/1994 (Tokukaihei No. 6-247981) has the following problems:

(1) since the reaction series must be kept at −65° C. or below, not only special equipment is required, but also the cooling cost is high;

(2) the process demands an expensive organic lithium compound (t-butyl lithium), which is a dangerous compound because it may ignite when reacted with water and the like;

(3) the process also demands expensive boron halide (boron trichloride), which is very difficult to handle because it is in the gaseous state and corrosive. Thus, the process disclosed in the above publication can not be readily adopted for industrial use.

In the process disclosed in U.S. Pat. No. 5,473,036, magnesium hydroxide is produced as a by-product with the object product, that is, the tetrakis(pentafluorophenyl)borate derivative. Since magnesium hydroxide turns a post-treatment solution into gel, it is difficult to separate (isolate) the tetrakis(pentafluorophenyl)borate derivative from the solution. Thus, there arises a problem that the tetrakis (pentafluorophenyl)borate derivative can not be produced efficiently.

In other words, the conventional producing processes have a problem that an inexpensive and highly-pure tetrakis (fluoroaryl)borate derivative can not be produced efficiently. Hence, there has been an increasing demand for a process of producing an inexpensive and highly-pure tetrakis (fluoroaryl)borate derivative efficiently.

Therefore, it is a first object of the present invention to provide a purifying process of separating/removing impurities, such as magnesium halide, from tetrakis (fluoroaryl)borate.magnesium halide readily and efficiently. Also, it is a second object of the present invention to provide a process of efficiently producing an inexpensive and highly-pure tetrakis (fluoroaryl)borate derivative, which is useful as, for example, a co-catalyst of the metallocene catalyst or a photopolymeric catalyst for silicone.

A process of producing tetrakis(pentafluorophenyl)borate, which is useful as an intermediate for producing the tetrakis (pentafluorophenyl)borate derivatives of various kinds, has been known.

For example, a process of obtaining tetrakis (pentafluorophenyl)borate.lithium by reacting pentafluorophenyl lithium, which is produced by reacting pentafluorophenyl bromide with butyl lithium at −78° C. in dry pentane, with tris(pentafluorophenyl)borate at −78° C. in dry pentane is disclosed in p245, J. Organometallic. Chem., 2, (1964).

Also, aforementioned Japanese Laid-open Patent Application No. 247981/1994 (Tokukaihei No. 6-247981) discloses a process of preparing tetrakis(pentafluorophenyl) borate.lithium used in the producing process of N,N-dimethyl anilinium.tetrakis(pentafluorophenyl)borate from N,N-dimethylaniline.hydrochloride as follows.

That is, the above publication discloses a process of preparing, in which pentafluorophenyl lithium is produced initially by reacting pentafluorophenyl bromide with t-butyl lithium at −65° C. in dry diethyl ether, and then tetrakis (pentafluorophenyl)borate.lithium is prepared by reacting the resulting pentafluorophenyl lithium with boron trichloride at −65° C. to −55° C. in dry pentane.

However, the process disclosed in p245, J. Organometallic. Chem., 2, (1964) has a problem that the yield of tetrakis(pentafluorophenyl)borate.lithium is low (43%). Also, since the process disclosed in aforementioned Japanese Laid-open Patent Application No. 247981/1994 (Tokukaihei No. 6-247981) has the above-explained problem, it can not be readily applied to industrial use.

On the other hand, aforementioned Japanese Laid-open Patent Application No. 247980/1994 (Tokukaihei No. 6-247980) discloses a process of obtaining the tetrakis (pentafluorophenyl)borate derivative by reacting pentafluorophenyl magnesium bromide, which is a Grignard reagent, with a boron trifluoride-diethyl ether complex.

Also, aforementioned U.S. Pat. No. 5,473,036 discloses a process of obtaining tetrakis(pentafluorophenyl) borate.magnesium bromide by reacting pentafluorophenyl magnesium bromide, which is a Grignard reagent, with a boron trifluoride.diethyl ether complex, and a process of obtaining N,N-dimethyl anilinium.tetrakis (pentafluorophenyl)borate by reacting tetrakis (pentafluorophenyl)borate.magnesium bromide with an aqueous solution of N,N-dimethylaniline.hydrochloride.

However, in the process disclosed in Japanese Laid-open Patent Application No. 247980/1994 (Tokukaihei No. 6-247980), magnesium halide, such as magnesium bromide fluoride (MgBrF), produced as a by-product with tetrakis (pentafluorophenyl)borate.magnesium bromide, is not separated/removed from the reaction series and remains therein as impurities. Thus, as previously mentioned, if the tetrakis(pentafluorophenyl)borate derivative is produced from tetrakis(pentafluorophenyl)borate.magnesium bromide containing magnesium halide as impurities and used as a co-catalyst of the metallocene catalyst, for example, the activity of the metallocene catalyst deteriorates considerably.

Further, in the processes disclosed in U.S. Pat. No. 398,236 and Japanese Laid-open Patent Application No. 247980/1994 (Tokukaihei No. 6-247980), resulting tetrakis (pentafluorophenyl)borate.magnesium bromide is colored with a coloring component derived from the Grignard reaction. Thus, if the tetrakis(pentafluorophenyl)borate derivative is produced from tetrakis(pentafluorophenyl) borate.magnesium bromide obtained in either of the above processes, there arises a problem that the coloring component remains in the tetrakis(pentafluorophenyl)borate derivative (the tetrakis(pentafluorophenyl)borate derivative is colored).

The process of producing tetrakis(pentafluorophenyl) borate derivative disclosed in U.S. Pat. No. 398,236 also has the following problem. That is, in the above process, a post-treatment solution is turned into gel by magnesium hydroxide produced as a by-product. Thus, it is difficult to filter the solution and isolate the tetrakis(pentafluorophenyl) borate derivative from the solution. Also, to isolate the tetrakis(pentafluorophenyl)borate derivative in the above process, a crude product must be crystallized again using a chlorine solvent, such as chloroform and dichloroethane.

As has been explained, since tetrakis(fluoroaryl) borate.magnesium bromide obtained by the conventional processes contains the by-product salts and coloring component as impurities, it can not be used as an adequate intermediate for producing the tetrakis (fluoroaryl)borate derivative. Hence, there has been an increasing demand for a tetrakis(fluoroaryl)borate derivative which can be used as a suitable intermediate for producing the tetrakis(fluoroaryl) borate derivatives of various kinds.

It is therefore a third object of the present invention to provide a tetrakis(fluoroaryl)borate.ether complex as a new material which can be used suitably as a co-catalyst of the metallocene catalyst, a cationic polymerization initiator, an intermediate for producing the tetrakis(fluoroaryl)borate derivatives of various kinds and the like, and a producing process of the same.

Also, the conventional producing processes of the tetrakis (fluoroaryl)borate derivative from tetrakis(fluoroaryl)borate prepared using an organic lithium compound or a Grignard reagent has a problem that an inexpensive and highly-pure tetrakis(fluoroaryl)borate derivative can not be produced efficiently.

It is therefore a fourth object of the present invention to provide a process of producing an inexpensive and highly-pure tetrakis(fluoroaryl)borate derivative efficiently. Also, it is a fifth object of the present invention to provide a process of producing highly-pure tetrakis(fluoroaryl)borate. Further, it is a sixth object of the present invention to provide a tetrakis(fluoroaryl)borate derivative.ether complex as a new material, which is useful not only as an intermediate for producing the tetrakis(fluoroaryl)borate derivative, but also as a co-catalyst of the metallocene catalyst (polymeric catalyst) used in the cationic complex polymerization reaction, and a process of producing the same. Furthermore, it is a seventh object of the present invention to provide a process of producing an inexpensive tetrakis(fluoroaryl) borate derivative from the tetrakis(fluoroaryl)borate derivative.ether complex efficiently.

To fulfill the first and second objects, the inventors of the present invention conducted an assiduous study on the process of purifying tetrakis(fluoroaryl)borate.magnesium halide and the process of producing the tetrakis(fluoroaryl) borate derivative. In due course, the inventors achieved the present invention when they discovered that:

the impurities, such as magnesium halide, can be readily and efficiently separated/removed from tetrakis (fluoroaryl)borate.magnesium halide by treating tetrakis(fluoroaryl)borate.magnesium halide with, for example, alkali metal salts of carboxylic acid and/or alkaline earth metal salts of carboxylic acid; and an inexpensive and highly-pure tetrakis(fluoroaryl)borate derivative, which is useful as, for example, a co-catalyst of the metallocene catalyst or a photopolymeric catalyst for silicone, can be produced efficiently by reacting a tetrakis(fluoroaryl)borate compound obtained through the above purifying process with a compound generating monovalent cationic compounds.

In other words, to fulfill the above objects, a process of purifying tetrakis(fluoroaryl)borate.magnesium halide of the present invention is characterized by treating tetrakis (fluoroaryl)borate.magnesium halide expressed by General Formula (1):

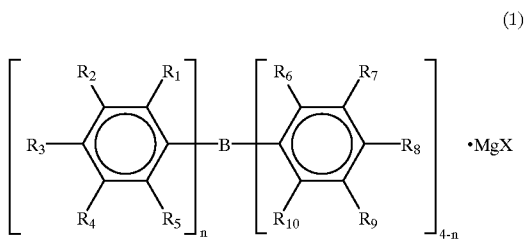

(1)

where each of $R_1$–$R_{10}$ represents a hydrogen atom, a fluorine atom, a hydrocarbon group, or an alkoxy group, provided that at least one of $R_1$–$R_5$ represents a fluorine atom and at least one of $R_6$–$R_{10}$ represents a fluorine atom, X represents a chlorine atom, a bromine atom, or an iodide atom, and n represents 2 or 3, with:

① alkali metal salts of carboxylic acid and/or alkaline earth metal salts of carboxylic acid;
② an acid;
③ an acid followed by alkali metal hydroxide and/or alkaline earth metal hydroxide; or
④ an acid followed by alkali metal salts of carboxylic acid and/or alkaline earth metal salts of carboxylic acid.

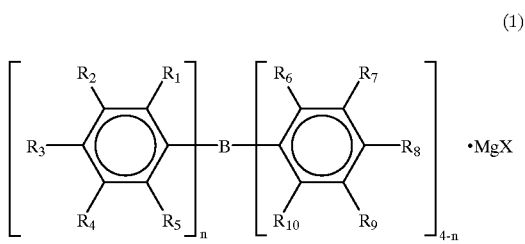

(1)

where each of $R_1$–$R_{10}$ represents a hydrogen atom, a fluorine atom, a hydrocarbon group, or an alkoxy group, provided that at least one of $R_1$–$R_5$ represents a fluorine atom and at least one of $R_6$–$R_{10}$ represents a fluorine atom, X represents a chlorine atom, a bromine atom, or an iodide atom, and n represents 2 or 3, with:

① alkali metal salts of carboxylic acid and/or alkali earth metal salts of carboxylic acid;
② an acid;
③ an acid followed by alkali metal hydroxide and/or alkali earth metal hydroxide; or
④ an acid followed by alkali metal salts of carboxylic acid and/or alkali earth metal salts of carboxylic acid.

According to the above process, magnesium halide, such as magnesium bromide fluoride, produced as a by-product during the producing process of tetrakis(fluoroaryl) borate.magnesium halide through the Grignard reaction can be turned into water-soluble or water-insoluble magnesium salts (that is, in the state of salts other than magnesium hydroxide). Thus, the salts can be readily and efficiently separated/removed from tetrakis(fluoroaryl) borate.magnesium halide through oil-water separation, filtration or the like. In short, the impurities, such as magnesium halide, can be readily and efficiently separated/removed from tetrakis(fluoroaryl)borate.magnesium halide.

When tetrakis(fluoroaryl)borate.magnesium halide is treated with the purifying process ①, ③ or ④, alkali metal salts and/or alkaline earth metal salts of tetrakis(fluoroaryl) borate can be obtained. When tetrakis(fluoroaryl) borate.magnesium halide is treated with the purifying process ②, hydrogen compound of tetrakis(fluoroaryl)borate can be obtained.

A process of producing a tetrakis(fluoroaryl)borate derivative of the present invention relates to a process of producing a tetrakis(fluoroaryl)borate derivative expressed by General Formula (2):

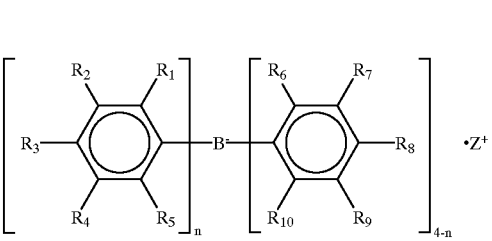

(2)

where each of $R_1$–$R_{10}$ represents a hydrogen atom, a fluorine atom, a hydrocarbon group, or an alkoxy group, provided that at least one of $R_1$–$R_5$ represents a fluorine atom and at least one of $R_6$–$R_{10}$ represents a fluorine atom, Z+ represents a monovalent cation seed, and n represents 2 or 3, and is characterized by reacting a tetrakis(fluoroaryl)borate compound obtained by any of the purifying processes ①–④ with a compound generating monovalent cation compounds.

According to the above process, an inexpensive tetrakis (fluoroaryl)borate derivative can be produced efficiently from the tetrakis(fluoroaryl)borate compound obtained through any of the above purifying processes, namely, alkali metal salts, alkaline earth metal salts, and hydrogen compounds of tetrakis(fluoroaryl)borate. The resulting tetrakis (fluoroaryl)borate derivative does not contain the impurities, such as magnesium halide, and therefore is so pure that it can be used suitably as, for example, a co-catalyst of the metallocene catalyst used in the cationic complex polymerization reaction or photopolymeric catalyst for silicone.

Also, to fulfill the third object, the inventors of the present invention conducted an assiduous study on the tetrakis (fluoroaryl)borate.ether complex and the process of producing the same. In due course, the inventors discovered that an inexpensive and highly-pure tetrakis(fluoroaryl)borate.ether complex as a new material, which can be suitably used as an intermediate for producing the tetrakis(fluoroaryl)borate derivatives of various kinds, can be obtained at high yield by reacting tetrakis(fluoroaryl)borate with a particular kind of ether compound.

In addition, the inventors achieved the present invention when they also discovered that even when tetrakis (fluoroaryl)borate.magnesium halide containing a coloring component derived from the Grignard reaction and by-product salts, such as magnesium bromide fluoride (MgBrF) produced as a by-product in the Grignard reaction, xis used as a raw material, that is, tetrakis(fluoroaryl)borate, a tetrakis(fluoroaryl)borate.ether complex can be obtained in the form of highly-pure crystals, from which the coloring component and by-product salts can be readily separated/removed.

In other words, a process of producing a tetrakis (fluoroaryl)borate.ether complex of the present invention relates to a process of producing a tetrakis(fluoroaryl) borate.ether complex expressed by Formula (4):

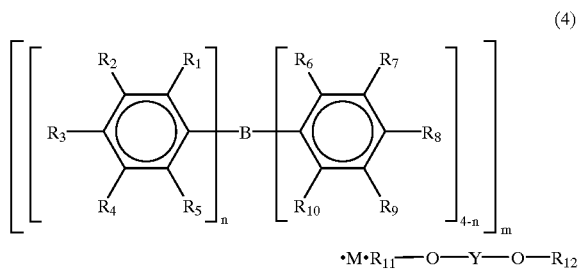

where each of $R_1$–$R_{10}$ represents a hydrogen atom, a fluorine atom, a hydrocarbon group, or an alkoxy group, provided that at least one of $R_1$–$R_5$ represents a fluorine atom and at least one of $R_6$–$R_{10}$ represents a fluorine atom, each of $R_{11}$ and $R_{12}$ represents a hydrocarbon group which may include a substituent group containing a hetero atom, Y represents a bivalent hydrocarbon group, M represents a hydrogen atom, alkali metal, alkaline earth metal, or alkaline earth metal halide, n represents 2 or 3, and m represents 1 when M represents a hydrogen atom, alkali metal, or alkaline earth metal halide, and 2 when M represents alkaline earth metal, and is characterized by reacting tetrakis(fluoroaryl)borate expressed by Formula (5):

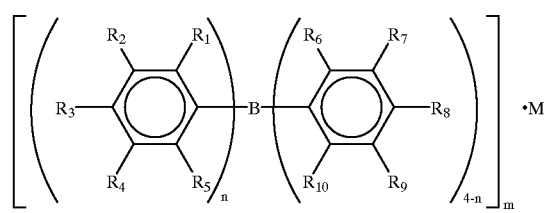

where each of $R_1$–$R_{10}$ represents a hydrogen atom, a fluorine atom, a hydrocarbon group, or an alkoxy group, provided that at least one of $R_1$–$R_5$ represents a fluorine atom and at least one of $R_6$–$R_{10}$ represents a fluorine atom, M represents a hydrogen atom, alkali metal, alkaline earth metal, or alkaline earth metal halide, n represents 2 or 3, and m represents 1 when M represents a hydrogen atom, alkali metal, or alkaline earth metal halide, and 2 when M represents alkaline earth metal, with an ether compound expressed by General Formula (6):

$R_{11}$—O—Y—O—$R_{12}$ (6)

where each of $R_{11}$ and $R_{12}$ represents a hydrocarbon group which may include a substituent group containing a hetero atom, and Y represents a hydrocarbon bivalent group.

According to the above process, an inexpensive and highly-pure tetrakis(fluoroaryl)borate.ether complex as a new material suitably used as, for example, a co-catalyst of the metallocene catalyst, a cationic polymerization initiator, or an intermediate for producing the tetrakis(fluoroaryl) borate derivatives of various kinds, can be produced at high yield.

Further, to fulfill the fourth through seventh objects, the inventors of the present invention conducted an assiduous study. In due course, the inventors achieved the present invention when they discovered that an inexpensive and highly-pure tetrakis(fluoroaryl)borate derivative can be produced efficiently when both a particular kind of tetrakis (fluoroaryl)borate.ether complex and a compound generating monovalent cationic compounds are used as a starting material.

Further, to fulfill the fourth through seventh objects, the inventors of the present invention conducted an assiduous study. In due course, the inventors achieved the present invention when they discovered that an inexpensive and highly-pure tetrakis(fluoroaryl)borate derivative can be produced efficiently when both a particular kind of tetrakis (fluoroaryl)borate.ether complex and a compound generating monovalent cation seeds are used as a starting material.

In other words, to fulfill the above objects, a process of producing the tetrakis(fluoroaryl)borate derivative of the present invention expressed by Formula (2) above is characterized by using both the tetrakis(fluoroaryl)borate.ether complex expressed by Formula (4) above and a compound generating monovalent cationic compounds as a starting material.

According to the above process, since the tetrakis (fluoroaryl)borate.ether complex expressed by General Formula (4) above, which can be readily and highly purified compared with tetrakis(fluoroaryl)borate, is used as the starting material, the tetrakis(fluoroaryl)borate derivative expressed by General Formula (2) above can be produced efficiently with high purity at low costs.

In addition, to fulfill the above objects, a process of producing tetrakis(fluoroaryl)borate expressed by Formula (5) above is characterized by removing the ether compound expressed by Formula (6) above from the tetrakis (fluoroaryl)borate.ether complex expressed by Formula (4) above.

According to the above processes, since the tetrakis (fluoroaryl)borate.ether complex expressed by General Formula (4) above, which can be readily and highly purified compared with tetrakis (fluoroaryl)borate, is used, highly-pure tetrakis(fluoroaryl)borate can be produced compared with the conventional process of producing tetrakis (fluoroaryl)borate directly from an organic lithium compound or a Grignard reagent.

Further, a process of producin g a tetrakis(fluoroaryl) borate derivative.ether complex of the present invention relates to a process of producing a tetrakis(fluoroaryl)borate derivative.ether complex expressed by General Formula (7):

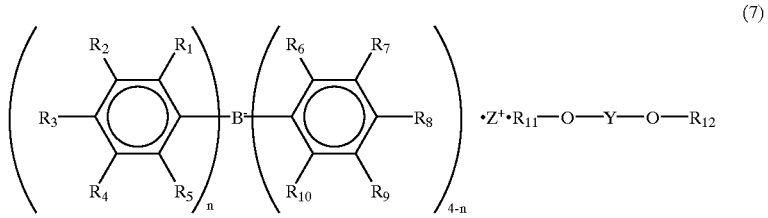

(7)

where each of $R_1$–$R_{10}$ represents a hydrogen atom, a fluorine atom, a hydrocarbon group, or an alkoxy group, provided that at least one of $R_1$–$R_5$ represents a fluorine atom and at least one of $R_6$–$R_{10}$ represents a fluorine atom, each of $R_{11}$ and $R_{12}$ represents a hydrocarbon group which may include a substituent group containing a hetero atom, Y represents a bivalent hydrocarbon group, Z+ represents a monovalent cationic compound, and n represents 2 or 3, and is characterized by reacting the tetrakis(fluoroaryl)borate.ether complex expressed by Formula (4) above with a compound generating monovalent cationic compounds.

According to the above process, the tetrakis(fluoroaryl) borate derivative.ether complex expressed as General Formula (7) above as a new, useful material for an intermediate in producing the tetrakis(fluoroaryl)borate derivative can be produced.

Further, to fulfill the above objects, a process of producing the tetrakis(fluoroaryl)borate derivative of the present invention expressed by Formula (2) above is characterized by removing the ether compound expressed by Formula (6) above from the tetrakis(fluoroaryl)borate derivative.ether complex expressed by Formula (7) above.

According to the above process, the tetrakis(fluoroaryl) borate derivative expressed by General Formula (2) above can be produced from the tetrakis(fluoroaryl)borate derivative.ether complex expressed by General Formula (7) above efficiently at low costs. DISCLOSURE OF THE INVENTION The purifying process of the tetrakis(fluoroaryl) borate.magnesium halide of the present invention expressed by General Formula (1) above is a process of applying the treatment with:

① alkali metal salts of carboxylic acid and/or alkaline earth metal salts of carboxylic acid;

② an acid;

③ an acid followed by alkali metal hydroxide and/or alkaline earth metal hydroxide; or ④ an acid followed by alkali metal salts of carboxylic acid and/or alkaline earth metal salts of carboxylic acid.

Also, the process of producing the tetrakis(fluoroaryl) borate derivative of the present invention expressed by Formula (2) above is a process of reacting a tetrakis (fluoroaryl)borate compound obtained by any of the purifying processes ①–④ with a compound generating monovalent cationic compounds.

Here, the tetrakis(fluoroaryl)borate compound means alkali salts, alkaline earth metal salts, and hydrogen compounds of tetrakis(fluoroaryl)borate. The tetrakis(fluoroaryl) borate.magnesium halide and tetrakis(fluoroaryl)borate compound are suitable as an intermediate of the tetrakis (fluoroaryl)borate derivative.

Tetrakis(fluoroaryl)borate.magnesium halide treated in the present invention is a compound, in which each of substituents denoted as $R_1$–$R_{10}$ is a hydrogen atom, a fluorine atom, a hydrocarbon group, or an alkoxy group, provided that at least one of $R_1$–$R_5$ is a fluorine atom and at least one of $R_6$–$R_{10}$ is a fluorine atom, a substituent denoted as X is a chlorine atom, a bromine atom, or an iodide atom, and n represents 2 or 3.

Examples of the hydrocarbon group include: aryl group, a straight-chain, branched-chain, or cyclic alkyl group having up to 12 carbon atoms, a straight-chain, branched-chain, or cyclic alkenyl group having 2–12 carbon atoms, etc. The hydrocarbon group may further include a functional group that remains inactive to the treatment carried out and reactions taking place in the present invention. Examples of the functional group include: a methoxy group, a methylthio group, an N,N-dimethylamino group, an o-anise group, a p-anise group, a trimethylsilyl group, a dimethyl-t-butyl silyloxy group, a trifluoromethyl group, etc.

The alkoxy group is expressed by General Formula (A):

—$OR_a$ (A)

where $R_a$ represents a hydrocarbon group. Examples of the hydrocarbon group denoted as $R_a$ in the formula are: an aryl group, a straight-chain, branched-chain, or cyclic alkyl group having up to 12 carbon atoms, a straight-chain, branched-chain, or cyclic alkenyl group having 2–12 carbon atoms. The hydrocarbon group may further include a functional group that remains inactive to the treatment carried out and reactions taking place in the present invention.

Examples of the alkoxy group expressed by General Formula (A) above are: a methoxy group, an ethoxy group, an n-propoxy group, an isopropoxy group, an n-butoxy group, an isobutoxy group, a sec-butoxy group, a t-butoxy group, a cyclohexyloxy group, an allyloxy group, a phenoxy group, etc.

Of all kinds of tetrakis(fluoroaryl)borate magnesium halide expressed by General Formula (1) above, the most preferred is tetrakis(pentafluorophenyl)borate.magnesium bromide.

A process of producing tetrakis(fluoroaryl) borate.magnesium halide is not especially limited. Tetrakis (fluoroaryl)borate.magnesium halide can be readily obtained by, for example: i) a process of reacting fluoroaryl magnesium halide as a Grignard reagent with boron halide in the mole ratio of 4:1; ii) a process of reacting fluoroaryl magnesium halide with tris(fluoroaryl)borane in the mole ratio of 1:1; etc. The reaction conditions of the Grignard reaction in these processes are not especially limited.

Tetrakis(fluoroaryl)borate.magnesium halide is obtained in the form of a solution dissolved into a solvent used in the Grignard reaction. Examples of the solvent include, but not limited to:

ether solvents, such as diethyl ether, diisopropyl ether, dibutyl ether, and anisole;

aliphatic hydrocarbon solvents, such as pentane, hexane, and heptane;

alicyclic hydrocarbon solvents, such as cyclopentane and cyclohexane;

aromatic hydrocarbon solvents, such as benzene and toluene; etc.

A mixture of these solvents can be used as well. In case that tetrakis(fluoroaryl)borate.magnesium halide is produced by reacting fluoroaryl magnesium halide with boron halide, magnesium halide, such as magnesium bromide fluoride, produced as a by-product is dissolved into the solution as the impurities.

Examples of the alkali metal salts of carboxylic acid used in the purifying process ① or ④ of the present invention include, but not limited to:

alkali metal salts of saturated aliphatic monocarboxylic acid, such as sodium formate, potassium formate, sodium acetate, potassium acetate, sodium propionate, and potassium propionate;

mono- or dialkali metal salts of saturated aliphatic dicarboxylic acid, such as sodium oxalate monobasic, sodium oxalate dibasic, potassium oxalate monobasic, potassium oxalate dibasic, sodium malonate monobasic, sodium malonate dibasic, potassium malonate monobasic, potassium malonate dibasic, sodium succinate monobasic, sodium succinate dibasic, potassium succinate monobasic, and potassium succinate dibasic;

alkali metal salts of unsaturated aliphatic monocarboxylic acid, such as sodium acrylate, potassium acrylate, sodium methacrylate, and potassium methacrylate;

mono- or dialkali metal salts of unsaturated aliphatic dicarboxylic acid, such as sodium maleate monobasic, sodium maleate dibasic, potassium maleate monobasic, potassium maleate dibasic, sodium fumarate monobasic, sodium fumarate dibasic, potassium fumarate monobasic, and potassium fumarate dibasic;

alkali metal salts of aromatic monocarboxylic acid, such as sodium benzoate and potassium benzoate;

mono- or dialkali metal salts of aromatic dicarboxylic acid, such as sodium phthalate monobasic, sodium phthalate dibasic, potassium phthalate monobasic, potassium phthalate dibasic, sodium isophthalate monobasic, sodium isophthalate dibasic, potassium isophthalate monobasic, potassium isophthalate dibasic, sodium terephthalate monobasic, sodium terephthalate dibasic, potassium terephthalate monobasic, and potassium terephthalate dibasic; etc. Note that, in the present invention, alkali metal salts of carboxylic acid include carbonates, such as lithium carbonate, sodium carbonate, sodium hydrocarbonate, potassium carbonate, and potassium hydrocarbonate.

Examples of the alkali earth metal salts of carboxylic acid used in the purifying process ① or ④ of the present invention include, but not limited to:

alkali earth metal salts of saturated aliphatic monocarboxylic acid, such as calcium formate, barium formate, calcium acetate, barium acetate, calcium propionate, and barium propionate;

alkali earth metal salts of saturated aliphatic dicarboxylic acid, such as calcium oxalate, barium oxalate, calcium malonate, barium malonate, calcium succinate, and barium succinate;

alkali earth metal salts of unsaturated aliphatic monocarboxylic acid, such as calcium acrylate, barium acrylate, calcium methacrylate, and barium methacrylate;

alkali earth metal salts of unsaturated aliphatic dicarboxylic acid, such as calcium maleate, barium maleate, calcium fumarate, and barium fumarate;

alkali earth metal salts of aromatic monocarboxylic acid, such as calcium benzoate and barium benzoate;

alkali earth metal salts of aromatic dicarboxylic acid, such as calcium phthalate, barium phthalate, calcium isophthalate, barium, isophthalate, calcium terephthalate, and barium terephthalate; etc.

In the present invention, the alkali earth metal salts of carboxylic acid include carbonates, such as calcium carbonate and barium carbonate. Note that, however, in the present invention, the alkali earth metal salts of carboxylic acid do not include magnesium salts of carboxylic acid.

One member or a mixture of two or more members selected from these examples of alkali metal salts of carboxylic acid and alkali earth metal salts of carboxylic acid (hereinafter, collectively referred to as carboxylate) can be used effectively. Of all the example carboxylates, lithium carbonate, sodium carbonate, potassium carbonate, sodium acetate, sodium succinate dibasic, and barium acetate are more preferable than the others. An amount of used carboxylate is not especially limited, but at least one equivalent of the carboxylate to tetrakis(fluoroaryl)borate.magnesium halide must be used. When a mixture of the alkali metal salts of carboxylic acid and alkali earth metal salts of carboxylic acid is used, a mixing ratio of these metal salts is not especially limited.

Examples of the acid used in the purifying process ②, ③, or ④ include, but not limited to:

inorganic acids, such as hydrochloric acid, sulfuric acid, nitric acid, phosphoric acid, and carbonic acid;

organic acids, such as formic acid, acetic acid, propionic acid, oxalic acid, malonic acid, and succinic acid; etc.

One member or a mixture of two or more members selected from these example acids can be used effectively. Of all these example acids, hydrochloric acid, sulfuric acid, formic acid, acetic acid, succinic acid, and malonic acid are more preferable than the others. An amount of used acid is not especially limited, but at least one equivalent of the acid to magnesium used (charged to the reaction series) when producing tetrakis(fluoroaryl)borate.magnesium halide must be used. In case that a mixture of the inorganic acid and organic acid is used, a mixing ratio of these acids is not especially limited.

Examples of alkali metal hydroxide used in the purifying process ③ of the present invention include lithium hydroxide, sodium hydroxide, potassium hydroxide, etc. Examples of alkali earth metal hydroxide used in the purifying process ③ of the present invention include calcium hydroxide, barium hydroxide, etc. Note that, however, in the present invention, alkali earth metal hydroxide does not include magnesium hydroxide.

One member or a mixture of two or more members selected from these example alkali metal hydroxides and alkali earth metal hydroxides (hereinafter, collectively referred to as hydroxide) can be used effectively. An amount of used hydroxide is not especially limited, but at least one equivalent of the hydroxide to tetrakis(fluoroaryl)borate.magnesium halide must be used. In case that a mixture of alkali metal hydroxide and alkali earth metal hydroxide is used, a mixing ratio of these hydroxides is not especially limited.

In case that tetrakis(fluoroaryl)borate.magnesium halide is treated with the carboxylate (purifying process ①), tetrakis(fluoroaryl)borate.magnesium halide is mixed with the carboxylate with stirring. In case that tetrakis(fluoroaryl)borate.magnesium halide is treated with the acid (purifying process ②), tetrakis(fluoroaryl)borate.magnesium halide is mixed with the acid with stirring. In case that tetrakis (fluoroaryl)borate.magnesium halide is treated with the acid followed by the hydroxide (purifying process ③), after the acid is separated/removed, tetrakis(fluoroaryl) borate.magnesium halide is mixed with the hydroxide with stirring. In case that tetrakis(fluoroaryl)borate.magnesium halide is treated with the acid followed by the carboxylate (purifying process ④), after the acid is separated/removed, tetrakis(fluoroaryl)borate.magnesium halide is mixed with the carboxylate with stirring.

A method of mixing a solution of tetrakis(fluoroaryl) borate.magnesium halide with the carboxylate, acid, or hydroxide is not especially limited. The carboxylate, acid, or hydroxide may be mixed with a solution of tetrakis (fluoroaryl)borate.magnesium halide directly (in the form of a solid or a liquid), or optionally, in the form of a solution.

Examples of preferable solvents when using a solution of the carboxylate, acid, or hydroxide include, but not limited to:

water;

ether solvents, such as diethyl ether, diisopropyl ether, dibutyl ether, and anisole;

aliphatic hydrocarbon solvents, such as pentane, hexane, and heptane;

alicyclic hydrocarbon solvents, such as cyclopentane and cyclohexane;

ester solvents, such as methyl acetate and ethyl acetate;

aromatic hydrocarbon solvents, such as benzene and toluene;

alcohol solvents, such as methyl alcohol and ethyl alcohol;

ketone solvents, such as acetone and methyl ethyl ketone; etc.

One member or a mixture: of two or more members selected from these example solvents can be used effectively.

A method of mixing tetrakis(fluoroaryl) borate.magnesium halide with the carboxylate, acid, or hydroxide, and a mixing order are not especially limited. For example, the carboxylate, acid, or hydroxide may be mixed a solution of tetrakis(fluoroaryl)borate.magnesium halide, or the solution of tetrakis(fluoroaryl)borate.magnesium halide may be mixed with the carboxylate, acid, or hydroxide.

A temperature and a time when mixing the solution of tetrakis(fluoroaryl)borate.magnesium halide with the carboxylate, acid, or hydroxide with stirring, that is, the treatment conditions, are not especially limited. According to the purifying processes ①–④ of the present invention, the solution of tetrakis(fluoroaryl)borate.magnesium halide is mixed with the carboxylate, acid, or hydroxide, after which the reaction solution is stirred for a certain time at room temperature, whereby tetrakis(fluoroaryl) borate.magnesium halide is readily treated. A method of separating/removing the acid when treating tetrakis (fluoroaryl)borate.magnesium halide with the acid followed by the hydroxide or carboxylate is not especially limited. For example, the acid can be readily separated from a solution of the tetrakis(fluoroaryl)borate compound by a simple manipulation, such as liquid separation (oil-water separation). After the treatment, the tetrakis(fluoroaryl) borate compound is obtained in the form of a solution dissolved into the solvent.

In case that the solution of the tetrakis(fluoroaryl)borate compound contains the carboxylate, acid, or hydroxide, the carboxylate, acid, or hydroxide can be removed optionally by washing or the like. In case that the carboxylate, acid, or hydroxide, or the solution thereof contains the tetrakis (fluoroaryl)borate compound, the tetrakis(fluoroaryl)borate compound can be collected optionally by extraction or the like. Further, in case that the solution of the tetrakis (fluoroaryl)borate compound contains water, water can be removed (dried out) optionally by adding a drying agent, such as magnesium sulfate anhydride.

A tetrakis(fluoroaryl)borate compound expressed by General Formula (3):

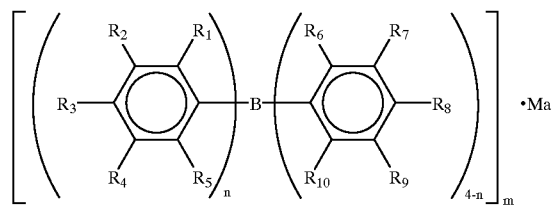

(3)

where each of $R_1$–$R_{10}$ represents a hydrogen atom, a fluorine atom, a hydrocarbon group, or an alkoxy group, provided that at least one of $R_1$–$R_5$ represents a fluorine atom and at least one of $R_6$–$R_{10}$ represents a fluorine atom, Ma represents a hydrogen atom, alkali metal, or alkaline earth metal, n represents 2 or 3, and m represents 1 when Ma represents a hydrogen atom or alkali metal, or 2 when Ma represents alkaline earth metal, can be obtained by treating tetrakis (fluoroaryl)borate.magnesium halide through any of the purifying processes ①–④.

In other words, when tetrakis(fluoroaryl) borate.magnesium halide is treated with the carboxylate or hydroxide, that is, through the purifying process ①, ③ or ④, tetrakis(fluoroaryl)borate expressed by Formula (3) above, in which Ma represents alkali metal or alkaline earth metal, can be obtained. Examples of alkali metal are lithium, sodium, potassium, etc. Examples of alkaline earth metal are calcium, barium, etc.

On the other hand, when tetrakis(fluoroaryl) borate.magnesium halide is treated with the acid, that is, through the purifying process ②, tetrakis(fluoroaryl)borate expressed by General Formula (3) above, in which Ma represents a, hydrogen atom, can be obtained.

Of all the purifying processes ①–④ of the present invention, the optimum purifying process can be selected depending on the kinds of tetrakis(fluoroaryl) borate.magnesium halide, solvents and the like, so that the resulting tetrakis(fluoroaryl)borate compound is in the desired form (alkali metal salts, alkaline earth metal salts, or hydride), or the post-treatment separatory manipulation, such as liquid separation, can be carried out more readily.

According to any purifying process of the present invention, for example, magnesium halide, which is produced as a by-product while tetrakis(fluoroaryl) borate.magnesium halide is produced through the Grignard reaction, can be converted to either water-soluble or water-insoluble magnesium salts (that is, salts other magnesium hydroxide). Thus, the salts contained in tetrakis(fluoroaryl) borate.magnesium halide can be separated/removed from the solution of the tetrakis(fluoroaryl)borate compound readily and efficiently through the manipulation, such as liquid separation and filtration. In short, the impurities, such as magnesium halide, can be separated/removed from tetrakis(fluoroaryl)borate.magnesium halide readily and efficiently. Here, a method of removing/separating the impurities from the solution of the tetrakis(fluoroaryl)borate compound is not especially limited.

When tetrakis(fluoroaryl)borate.magnesium halide does not contain the impurities, such as magnesium halide, it is preferable to obtain the hydrogen compound, alkali metal salts, or alkaline earth metal salts of tetrakis(fluoroaryl) borate through the above treatment. Because, by applying the above treatment, the reaction with a compound generating monovalent cationic compounds can proceed faster and at higher yield.

As has been explained, the purifying processes of tetrakis (fluoroaryl)borate.magnesium halide of the present invention are:

① a process of treating tetrakis(fluoroaryl) borate.magnesium halide with carboxylate;

② a process of treating tetrakis(fluoroaryl) borate.magnesium halide with an acid;

③ a process of treating tetrakis(fluoroaryl) borate.magnesium halide with an acid followed by the hydroxide; and ④ a process of treating tetrakis(fluoroaryl) borate.magnesium halide with an acid followed by the carboxylate.

Consequently, it has become possible to provide a purifying process of separating/removing the impurities, such as magnesium halide, from tetrakis(fluoroaryl) borate.magnesium halide readily and efficiently. Also, for example, the reaction of the tetrakis(fluoroaryl)borate compound obtained by the above purifying process with a compound generating monovalent cationic compounds can proceed faster at higher yield. The tetrakis(fluoroaryl)borate compound can be isolated/purified in the form of crystals by removing (distilling out) the solvent optionally.

The compound generating monovalent cationic compounds referred herein (hereinafter, referred to as cationic compound generating compound) can be any compound which generates monovalent cationic compounds in a reaction solvent described below and is reactive with either the tetrakis (fluoroaryl)borate compound or the tetrakis (fluoroaryl)borate.ether complex or tetrakis(fluoroaryl) borate (the compound will be described below).

Examples of the monovalent cationic compounds generated by the cationic compound seed generating compound include, but not limited to:

ammonium cations, such as n-butyl ammonium, dimethyl ammonium, trimethyl ammonium, triethyl ammonium, triisopropyl ammonium, tri-n-butyl ammonium, tetramethyl ammonium, tetraethyl ammonium, and tetra-n-butyl ammonium;

anilinium cations, such as anilinium, N-methyl anilinium, N,N-dimethyl anilinium, N,N-diethyl anilinium, N,N-diphenyl anilinium, and N,N,N-trimethyl anilinium;

pyridinium cations, such as pyridinium, N-methyl pyridinium, and N-benzyl pyridinium;

quinolinium cations, such as quinolinium and isoquinolinium;

phosphonium cations, such as dimethylphenyl phosphonium, triphenyl phosphonium, tetraethyl phosphonium, and tetraphenyl phosphonium;

sulfonium cations, such as trimethyl sulfonium and triphenyl sulfonium;

iodonium cations, such as diphenyl iodonium and di-4-methoxy phenyl iodonium;

carbenium cations, such as triphenyl carbenium and tri-4-methoxyphenyl carbenium;

monovalent cations of metals other than alkali metal and alkaline earth metal; etc.

Of all these examples, trialkyl ammonium cation, tetraalkyl ammonium cation, dialkyl anilinium cation, alkylpyridinium cation, tetraalkyl phosphonium cation, tetraaryl phosphonium cation, and diaryl iodonium cation are more preferable than the others. Here, anion seeds that form a pair with the monovalent cationic compounds are not especially limited.

Examples of the cation seed generating compound include:

quaternary ammonium compounds, such as tri-n-butylamine.hydrochloride, N,N-dimethylaniline.hydrochloride, N,N-dimethylaniline.sulfate, and tetramethyl ammonium chloride;

nitrogen-containing aromatic heterocyclic compounds, such as pyridine.hydrochloride, quinoline.hydrochloride, N-methyl pyridine iodide, and N-methyl quinoline iodide;

quaternary phosphonium compounds, such as n-butylphosphonium bromide and tetraphenyl phosphonium bromide;

sulfonium compounds, such as trimethyl sulfonium iodide;

iodinium compounds, such as diphenyl iodinium chloride;

carbenium compounds, such as trityl chloride; etc.

For example, N,N-dimethylaniline.hydrochloride generates N,N-dimethyl anilinium cations as the monovalent cation seeds. In this case, the anion seeds are chlorine ions.

An amount of used cationic compound generating compound is not especially limited, but at least 0.8 equivalent of cationic compound generating compound to the tetrakis (fluoroaryl)borate compound, a tetrakis (fluoroaryl) borate.ether complex described below, or tetrakis (fluoroaryl)borate must be used.

The producing process of the tetrakis(fluoroaryl)borate derivative of the present invention uses a reaction solvent. Examples of the reaction solvent include, but not limited to:

water;

ether solvents, such as diethyl ether, diisopropyl ether, dibutyl ether, and anisole;

aliphatic hydrocarbon solvents, such as pentane, hexane, and heptane;

alicyclic hydrocarbon solvents, such as cyclopentane and cyclohexane;

ester solvents, such as methyl acetate and ethyl acetate;

aromatic hydrocarbon solvents, such as benzene and toluene;

alcohol solvents, such as methyl alcohol and ethyl alcohol;

ketone solvents, such as acetone and methyl ethyl ketone; etc.

One member or a mixture of two or more members selected from these example reaction solvents can be used effectively.

In case that the solution of the tetrakis(fluoroaryl)borate compound obtained by the above treatment is used for the reaction, a solvent, in which the tetrakis(fluoroaryl)borate compound is dissolved, can be used as the reaction solvent (either entirely or partially). Thus, in the producing process of the tetrakis(fluoroaryl)borate derivative of the present invention, after tetrakis(fluoroaryl)borate.magnesium halide is treated, the tetrakis(fluoroaryl)borate derivative can be produced from the resulting solution of the tetrakis (fluoroaryl)borate compound without isolating the tetrakis (fluoroaryl)borate compound from the solution.

Exemplary mixing methods of the tetrakis(fluoroaryl) borate compound with the cationic compound generating compound include, but not limited to:

a method of mixing the tetrakis(fluoroaryl)borate compound and cationic compound generating compound with the reaction solvent;

a method of mixing the cationic compound generating compound or a solution thereof with a solution of the tetrakis(fluoroaryl)borate compound;

a method of mixing the tetrakis(fluoroaryl)borate compound or a solution thereof with a solution of the cationic compound generating compound; etc. In case that the solution of the cationic compound generating compound is mixed with the solution of the tetrakis (fluoroaryl)borate compound, and the solution of the tetrakis(fluoroaryl)borate compound is mixed with the solution of the cationic compound generating compound, it is preferable to drop the former to the latter.

A temperature and a time in the reaction of the tetrakis (fluoroaryl)borate compound with the cationic compound generating compound, that is, the reaction conditions, are not especially limited. In the process of the present invention, the reaction can proceed readily by stirring a reaction liquid, prepared by dissolving the tetrakis (fluoroaryl)borate compound and the cationic compound generating compound into the reaction solvent, for a certain time at room temperature. Thus, the object product, that is, the tetrakis(fluoroaryl)borate derivative, can be readily obtained.

For example, when the tetrakis(fluoroaryl)borate compound is the alkali metal salts or alkaline earth metal salts of tetrakis(fluoroaryl)borate and the cationic compound generating compound is N,N-dimethylaniline.hydrochloride, the object product, that is, N,N-dimethyl anilinium.tetrakis (fluoroaryl)borate can be obtained by reacting the above two compounds with each other, while alkali metal chloride, such as sodium chloride, or alkaline earth metal chloride, such as calcium chloride, is produced as a by-product. The alkali metal chloride or alkaline earth metal chloride can be readily separated/removed from the solution of N,N-dimethyl anilinium.tetrakis(fluoroaryl)borate through the manipulation, such as liquid separation, filtration, and washing.

For example, when the tetrakis(fluoroaryl)borate compound is a hydrogen compound of tetrakis(fluoroaryl)borate and the cation seed generating compound is N,N-dimethylaniline.hydrochloride, the object product, that is, N,N-dimethyl anilinium.tetrakis(fluoroaryl)borate can be obtained by reacting the above two compounds with each other, while hydrochloric acid is produced as a by-product. The hydrochloric acid can be readily separated/removed from N,N-dimethyl anilinium.tetrakis(fluoroaryl)borate through the manipulation, such as liquid separation and washing.

In short, the tetrakis(fluoroaryl)borate derivative can be readily isolated/purified as crystals through an optional simple manipulation, such as removal (distillation) of the reaction solvent, after a simple manipulation, such as liquid separation and filtration.

As has been explained, the process of producing the tetrakis(fluoroaryl)borate derivative of the present invention is a process of reacting the tetrakis(fluoroaryl)borate compound obtained by any of the above purifying processes with the cationic compound generating compound.

According to the above process, the tetrakis(fluoroaryl) borate derivative can be produced efficiently at low costs from the tetrakis(fluoroaryl)borate compound, namely, alkali metal salts, alkaline earth metal salts, and hydrogen compound of tetrakis(fluoroaryl)borate. Since the resulting derivative does not contain the impurities, such as magnesium halide, the derivative is so pure that it can be suitably used as a co-catalyst of the metallocene catalyst used in the cationic complex polymerization reaction or a photopolymeric catalyst for silicone.

A producing process of the tetrakis(fluoroaryl) borate.ether complex of the present invention is a process of reacting tetrakis(fluoroaryl)borate expressed by General Formula (5) above with the ether compound expressed by General Formula (6) above. Consequently, the tetrakis (fluoroaryl)borate.ether complex of the present invention expressed by General Formula (4) above can be obtained.

Tetrakis(fluoroaryl)borate expressed by General Formula (5) above and used in the above process is a compound, in which each of the substituents denoted as $R_1$–$R_{10}$ is a hydrogen atom, fluorine atom, a hydrocarbon group or an alkoxy group, provided that at least one of the substituents denoted as $R_1$–$R_5$ is a fluorine atom and at least one of the substituents denoted as $R_6$–$R_{10}$ is a fluorine atom, a substituent denoted as M is a hydrogen atom, alkali metal, alkaline earth metal, or alkaline earth metal halide, n is 2 or 3, and m is 1 when M is a hydrogen atom, alkali metal, or alkaline earth metal halide, and 2 when M is alkaline earth metal. Examples of alkaline earth metal halide include magnesium chloride, magnesium bromide, magnesium iodide, etc.

In other words, tetrakis(fluoroaryl)borate expressed by General Formula (5) above includes both the tetrakis (fluoroaryl)borate compound expressed by General Formula (3) above and tetrakis(fluoroaryl)borate.magnesium halide expressed by General Formula (1) above.

Of all the examples of tetrakis(fluoroaryl)borate expressed by Formula (5) above, tetrakis (pentafluorophenyl)borate.magnesium bromide, tetrakis (pentafluorophenyl)borate.lithium, tetrakis (pentafluorophenyl)borate.sodium, and tetrakis (pentafluorophenyl)borate.potassium are particularly preferred. Note that a process of producing tetrakis (fluoroaryl)borate is not limited to the above disclosure.

The ether compound expressed by Formula (6) above and used in the process of the present invention is a compound, in which each of the substituents denoted as $R_{11}$l and $R_{12}$ is a hydrocarbon group which may include a substituent containing a hetero atom, and a substituent denoted as Y is a bivalent hydrocarbon group.

Examples of the hydrocarbon group include an alkyl group, an aryl group, a cycloalkyl group, a benzyl group, etc. However, an alkyl group having up to 10 carbon atoms and an aryl group are particularly preferred. Examples of the substituent containing a hetero atom include:

substituents containing oxygen atoms, such as an alkoxy group, an aryloxy group, a cycloalkyloxy group, and an acyloxy group;

substituents containing nitrogen atoms, such as a dialkyl amino group;

substituents containing sulfur atoms, such as an alkylthio group and an arylthio group; etc.

The hydrocarbon bivalent group is preferably a bivalent group selected from the group consisting of an alkylene group having up to six carbon atoms as a carbon chain linking two oxygen atoms, namely, a methylene group possibly having a substituent, an ethylene group possibly having a substituent, a trimethylene group possibly having a substituent, a tetramethylene group possibly having a substituent, a pentamethylene group possibly having a substituent, and a hexamethylene group possibly having a substituent. It is more preferable that the substituent in the bivalent group is an alkyl group having up to six carbon atoms.

Examples of the ether compound expressed by General Formula (6) above (hereinafter, referred to as polyfunctional ether) include:

ethylene glycol dialkyl ether, such as 1,2-dimethoxy ethane, 1,2-diethoxy ethane, ethylene glycol di-n-propyl ether, ethylene glycol diisopropyl ether, ethylene glycol di-n-butyl ether, ethylene glycol diisobutyl ether, ethylene glycol di-sec-butyl ether, ethylene glycol di-t-butyl ether, ethylene glycol dipentyl ether, ethylene glycol dineopentyl ether, ethylene glycol dihexyl ether, ethylene glycol diheptyl ether, ethylene glycol dioctyl ether, ethylene glycol dinonyl ether, and ethylene glycol didecyl ether;

ethylene glycol dicycloalkyl ether, such as ethylene glycol dicyclopropyl ether, ethylene glycol dicyclo butyl ether, ethylene glycol dicyclopentyl ether, ethylene glycol dicyclohexyl ether, ethylene glycol diheptyl ether, ethylene glycol dicyclo octyl ether, ethylene glycol dicyclo nonyl ether, and ethylene glycol dicyclo decyl ether;

unsymetric ethylene glycol methyl alkyl ether, such as ethylene glycol methyl ethyl ether, ethylene glycol methyl isopropyl ether, and ethylene glycol methyl butyl ether;

diethylene glycol dialkyl ether, such as diethylene glycol dimethyl ether, diethylene glycol diethyl ether, diethylene glycol diisopropyl ether, diethylene glycol dibutyl ether, diethylene glycol dipentyl ether, diethylene glycol dihexyl ether, diethylene glycol diheptyl ether, diethylene glycol dioctyl ether, diethylene glycol dinonyl ether, and diethylene glycol didecyl ether;

triethylene glycol dialkyl ether, such as triethylene glycol dimethyl ether, triethylene glycol diethyl ether, triethylene glycol diisopropyl ether, triethylene glycol dibutyl ether, triethylene glycol dipentyl ether, triethylene glycol dihexyl ether, triethylene glycol diheptyl ether, triethylene glycol dioctyl ether, triethylene glycol dinonyl ether, and triethylene glycol didecyl ether;

ethylene glycol dialkyl ether having an acyloxy group, such as diethylene glycol monoethyl ether acetate and diethylene glycol monoethyl ether methacrylate;

ethylene glycol dialkyl ether having an alkylthio group, such as ethylene glycol, di-2-methylthio ethyl ether;

ethylene glycol dialkyl ether having a dialkyl amino group, such as ethylene glycol di-2-dimethyl amino ethyl ether;

ethylene glycol diaryl ether, such as ethylene glycol diphenyl ether;

diethylene glycol diaryl ether, such as diethylene glycol diphenyl ether;

triethylene glycol diaryl ether, such as triethylene glycol diphenyl ether;

ethylene glycol dibenzyl ether; etc.

It is preferable that the polyfunctional ether is in the state of liquid at room temperature. However, even if the polyfunctional ether is in the state of solid at room temperature, it can be melted into a liquid with heating. Of all these example compounds, 1,2-dimethoxy ethane, 1,2-diethoxy ethane, and diethylene glycol dimethyl ether are particularly preferred because they can be readily converted into highly-pure tetrakis(fluoroaryl)borate through distillation; moreover, they are inexpensive and readily available for industrial use.

The amount of polyfunctional ether used is not especially limited, but it is preferable to use a mole equivalent of polyfunctional ether to tetrakis(fluoroaryl)borate, because tetrakis(fluoroaryl)borate and the polyfunctional ether form the complex when their mole ratio is 1:1 or greater. In the process of producing the tetrakis(fluoroaryl)borate.ether complex of the present invention, a method of reacting tetrakis(fluoroaryl)borate with the polyfunctional ether is not especially limited, but a method of mixing tetrakis (fluoroaryl)borate with the polyfunctional ether in a solvent is suitable.

The solvent used in the above reaction can be any solvent generally used for organic synthesis, and is not especially limited. Examples of the solvent include: organic solvents, such as aliphatic hydrocarbon solvents, alicyclic hydrocarbon solvents, alcohol solvents, ketone solvents, ester solvents, aromatic hydrocarbon solvents, and ether solvents; water; etc. One member or a mixture of two or more members selected from these example solvents can be used effectively.

Of all these example solvents, particularly preferred are the solvents with which the solubility of the tetrakis (fluoroaryl)borate.ether complex is relatively low, namely:

ether solvents, such as diethyl ether, diisopropyl ether, dibutyl ether, and anisole;

aliphatic hydrocarbon solvents, such as pentane, hexane, and heptane;

alicyclic hydrocarbon solvents, such as cyclopentane and cyclohexane;

ester solvents, such as methyl acetate and ethyl acetate;

aromatic hydrocarbon solvents, such as benzene and toluene; etc.

When these solvents are used, the tetrakis(fluoroaryl) borate.ether complex can be readily crystallized and therefore, readily separated from the solution.

When the solvents with which the solubility of the tetrakis (fluoroaryl)borate.ether complex is high, for example, alcohol solvents, such as methyl alcohol and ethyl alcohol or ketone solvents, such as acetone and methyl ethyl ketone, are used, the tetrakis(fluoroaryl)borate.ether complex does not crystalize after the formation. Thus, in this case, the solvent is distilled out. Note that polar solvents, such as nitromethane and acetonitrile, are not preferable, because they have higher coordination strength than the polyfunctional ethers and inhibit the formation of the ether complex.

An amount of used solvent is not especially limited, but when the tetrakis(fluoroaryl)borate.ether complex alone is crystallized and taken out from the reaction series, it is preferable to use the solvent sufficiently, so that tetrakis (fluoroaryl)borate is dissolved therein completely. Consequently, when the complex is formed using tetrakis (fluoroaryl)borate containing a coloring component or by-product salts, the coloring component or by-product salts remain in the reaction series, and for this reason, a highly-pure colorless tetrakis(fluoroaryl)borate.ether complex can be obtained through the manipulation, such as filtration.

An amount of used solvent does not have to be sufficient to dissolve tetrakis(fluroaryl)borate completely. For example, the complex can be formed if the reaction takes place in the suspended state. In this case, tetrakis(fluoroaryl) borate is reacted with the polyfunctional ether in the suspended state, and the resulting tetrakis(fluoroaryl) borate.ether complex is taken out from the reaction series through filtration or the like. In case that the tetrakis (fluoroaryl)borate.ether complex thus taken out contains the impurities, such as the coloring component and by-product salts, it is preferable to wash the tetrakis(fluoroaryl) borate.ether complex with an adequate solvent (for example, ether solvents) that can dissolve these impurities. Consequently, a highly-pure colorless tetrakis (fluoroaryl) borate.ether complex can be obtained.

Alternatively, after the tetrakis(fluoroaryl)borate.ether complex is formed by reacting tetrakis(fluoroaryl)borate with excessive polyfunctional ether without using the solvent, the excessive polyfunctional ether that does not form the complex may be distilled out. In case that the resulting product contains the impurities, such as the coloring component and by-product salts, it is preferable to wash the resulting product with an adequate solvent (for example, ether solvents) which can dissolve these impurities.

A method of mixing tetrakis(fluoroaryl)borate with the polyfunctional ether and a mixing order thereof are not especially limited. Example mixing methods are: a method of adding the polyfunctional ether to a solution of tetrakis (fluoroaryl)borate; a method of adding a solution of tetrakis (fluoroaryl)borate to the polyfunctional ether; etc.

The reaction temperature is not especially limited, but it is preferably at or below the boiling point of the polyfunctional ether. When the solvent is additionally used, it is further preferable that the reaction temperature is at or below the boiling point of the solvent.

The reaction of tetrakis(fluoroaryl)borate and the polyfunctional ether takes place very fast in a mixed rate-determining manner, but a time is required for the formed complex to grow to crystals. Thus, the reaction time can be set to at least as long as the time necessary for the formed complex to grow to crystals. Further, the reaction can take place under normal, reduced, or applied pressure.

The tetrakis(fluoroaryl)borate.ether complex can be obtained by the above process. In case that the resulting tetrakis(fluoroaryl)borate.ether complex contains the impurities, such as the coloring component and by-product salts, the resulting complex can be readily purified to a high level when washed with an adequate solvent (for example, ether solvent) that dissolves these impurities. Hence, the complex can be used as an excellent starting material of the tetrakis(fluoroaryl)borate derivative.

A process of producing the tetrakis(fluoroaryl)borate derivative of the present invention expressed by General Formula (2) above is a process, in which both the tetrakis (fluoroaryl)borate.ether complex and the aforementioned cationic compound generating compound are used as the starting material. Also, the above process includes a step of removing the polyfunctional ether from the reaction series. In the above producing process, the tetrakis(fluoroaryl) borate.ether complex or tetrakis(fluoroaryl)borate is reacted with the cationic compound generating compound in the aforementioned reaction solvent.

In other words, a process of producing the tetrakis (fluoroaryl)borate derivative of the present invention includes two types of processes:
  a first process, in which, after tetrakis(fluoroaryl)borate is obtained by removing the polyfunctional ether from the tetrakis(fluoroaryl)borate.ether complex, the resulting tetrakis(fluoroaryl)borate is reacted with the cationic compound generating compound;
  a second process, in which, after the tetrakis(fluoroaryl) borate derivative.ether complex is obtained by reacting the tetrakis(fluoroaryl)borate.ether complex with the cationic compound generating compound, the polyfunctional ether is removed from the resulting tetrakis (fluoroaryl)borate derivative.ether complex.

In the first process, it is preferable that a first step of removing the polyfunctional ether from the tetrakis (fluoroaryl)borate.ether complex is carried out by heating the tetrakis(fluoroaryl)borate.ether complex in a reaction vessel, so that the polyfunctional ether is distilled out from the reaction vessel.

The heating temperature is not especially limited as long as the polyfunctional ether can be removed from the tetrakis (fluoroaryl)borate.ether complex. However, a preferable temperature is 40° C. or above, and a range between 40° C. and 200° C. is further preferable. A heating time is not especially limited, either.

To distill out the polyfunctional ether from the reaction vessel, the temperature inside the reaction vessel must be raised higher than the boiling point of the polyfunctional ether under the current pressure inside the reaction vessel. Thus, the pressure inside the reaction vessel may be reduced optionally. Consequently, the polyfunctional ether can be distilled out at a relatively low temperature.

Also, in the first step, the tetrakis(fluoroaryl)borate.ether complex can be in the form of a solution dissolved into the solvent, or suspended in the solvent.

In the first producing process, if the first step of removing the polyfunctional ether from the tetrakis(fluoroaryl) borate.ether complex is carried out solely, in other words, if a second step is not carried out, the producing process is same as the producing process of tetrakis(fluoroaryl)borate. According to the above process, inexpensive and highly-pure tetrakis(fluoroaryl)borate can be produced efficiently.

In the first process, the second step of reacting the resulting tetrakis(fluoroaryl)borate with the cationic compound generating compound is carried out in the aforementioned reaction solvent.

In case that the reaction is carried out using a solution of tetrakis(fluoroaryl)borate, a solution in which tetrakis (fluoroaryl)borate is dissolved can be used as the reaction solvent (either entirely or partially). Thus, the tetrakis (fluoroaryl)borate derivative can be produced using the solution of the tetrakis(fluoroaryl)borate obtained in the first step without isolating the compound from the solution.

A method of mixing tetrakis(fluoroaryl)borate with the cationic compound generating compound is not especially limited, and examples of which are: a method of mixing tetrakis(fluoroaryl)borate and the cation seed generating compound with the reaction solvent; a method of mixing the cationic compound generating compound or a solution thereof with a solution of tetrakis(fluoroaryl)borate; a method of mixing tetrakis(fluoroaryl)borate or a solution thereof with a solution of the cationic compound generating compound; etc. In case that the solution of the cationic compound generating compound is mixed with the solution of tetrakis(fluoroaryl)borate, and the solution of tetrakis (fluoroaryl)borate is mixed with the solution of the cationic compound generating compound, it is preferable to drop the former to the latter.

A reaction temperature and a reaction time in the reaction of tetrakis(fluoroaryl)borate and the cationic compound generating compound, that is, the reaction conditions, are not especially limited. In the producing process of the present invention, the reaction is allowed to readily proceed by stirring a reaction liquid, prepared by dissolving tetrakis (fluoroaryl)borate and the cationic compound generating compound into the reaction solvent, for a certain time at room temperature. Consequently, the object product, that is, the tetrakis(fluoroaryl)borate derivative, can be readily obtained.

For example, when the tetrakis(fluoroaryl)borate is alkali metal salts or alkaline earth metal salts of tetrakis (fluoroaryl)borate, and the cationic compound generating compound is N,N-dimethylaniline.hydrochloride, the object product, that is, N,N-dimethyl anilinium.tetrakis(fluoroaryl) borate, can be obtained by reacting the above two compounds with each other, while alkali metal chloride, such as sodium chloride, or alkaline earth metal chloride, such as calcium chloride, is produced as a by-product. The alkali metal chloride or alkaline earth metal chloride can be readily separated/removed from the solution of N,N-dimethyl anilinium.tetrakis(fluoroaryl)borate through the manipulation, such as liquid separation, filtration, and washing. When the reaction solvent is water, the alkali metal chloride or alkaline earth metal chloride can be readily removed by filtering N,N-dimethyl anilinium.tetrakis (fluoroaryl)borate followed by the washing with water.

Also, for example, when the tetrakis(fluoroaryl)borate is tetrakis(fluoroaryl)borate.magnesium halide, and the cationic compound generating compound is N,N-dimethylaniline.hydrochloride, the object product, that is, N,N-dimethyl anilinium.tetrakis(fluoroaryl)borate, can be obtained by reacting the above two compounds with each other, while magnesium halide, such as magnesium bromide chloride, is produced as a by-product.

The magnesium halide can be readily separated/removed from N,N-dimethyl anilinium.tetrakis(fluoroaryl)borate through the manipulation, such as liquid separation, filtration, and washing. To be more specific, magnesium bromide chloride can be readily separated/removed by being washed with an acidic aqueous solution, such as hydrochloric acid, or being reacted with N,N-dimethylaniline hydrochloride containing excessive hydrochloric acid followed by the washing with water.

In the second Process, a first step of reacting the tetrakis (fluoroaryl)borate.ether complex with the cationic compound generating compound is carried out in the aforementioned reaction solvent.

In the second producing Process, a first step of reacting the tetrakis(fluoroaryl)borate.ether complex with the cation seed generating compound is carried out in the aforementioned reaction solvent.

A method of mixing the tetrakis(fluoroaryl)borate.ether complex with the cationic compound generating compound is not especially limited, and examples of which are: a method of mixing the tetrakis(fluoroaryl)borate.ether complex and the cationic compound generating compound with the reaction solvent; a method of mixing the cationic compound generating compound or a solution thereof with a solution of the tetrakis(fluoroaryl)borate.ether complex; a method of mixing the tetrakis(fluoroaryl)borate.ether complex or a solution thereof with a solution of the cationic compound generating compound; etc. In case that the solution of the cationic compound generating compound is mixed with the solution of the tetrakis(fluoroaryl) borate.ether complex, and the solution of the tetrakis (fluoroaryl)borate.ether complex is mixed with the solution of the cationic compound generating compound, it is preferable to drop the former to the latter.

A reaction temperature and a reaction time in the reaction of the tetrakis(fluoroaryl)borate.ether complex and the cationic compound generating compound, that is, the reaction conditions, are not especially limited. In the producing process of the present invention, the reaction is allowed to readily proceed by stirring a reaction liquid made by dissolving or suspending the tetrakis(fluoroaryl)borate.ether complex and the cationic compound generating compound into the reaction solvent for a certain time at or below the boiling point. Consequently, the object product, that is, the tetrakis(fluoroaryl)borate derivative.ether complex, can be readily obtained.

For example, when the tetrakis(fluoroaryl)borate.ether complex is a tetrakis(fluoroaryl)borate.alkali metal salts.ether complex or a tetrakis(fluoroaryl)borate.alkaline earth metal salts.ether complex, and the generating compound is N,N-dimethylaniline.hydrochloride, the object product, that is, N,N-dimethyl anilinium.tetrakis(fluoroaryl)borate.ether complex, can be obtained by reacting the above two compounds with each other, while alkali metal chloride, such as sodium chloride, or alkaline earth metal chloride, such as calcium chloride, is produced as a by-product. The alkali metal chloride or alkaline earth metal chloride can be readily separated/removed from a solution of N,N-dimethyl anilinium.tetrakis(fluoroaryl)borate.ether complex through the manipulation, such as liquid separation, filtration, and washing. More specifically, the alkali metal chloride can be separated/removed readily by being washed with water.

Also, for example, when the tetrakis(fluoroaryl) borate.ether complex is tetrakis(fluoroaryl) borate.magnesium halide-ether complex, and the cationic compound generating compound is N,N-dimethylaniline.hydrochloride, the object product, that is, N,N-dimethyl anilinium.tetrakis(fluoroaryl)borate.ether complex, can be obtained by reacting the above two compounds with each other, while magnesium halide, such as magnesium bromide chloride, is produced as a by-product.

The magnesium halide can be readily separated/removed from the N,N-dimethyl anilinium.tetrakis(fluoroaryl) borate.ether complex through the manipulation, such as liquid separation, filtration, and washing. More specifically, for example, magnesium bromide chloride can be readily separated/removed by being washed with an acidic aqueous solution, such as hydrochloric acid, or being, reacted with N,N-dimethylaniline.hydrochloride containing excessive hydrochloric acid followed by the washing with water.

In short, the tetrakis(fluoroaryl)borate derivative.ether complex can be readily isolated/purified as crystals through an optional simple manipulation, such as removal (distillation) of the reaction solvent or the like after a simple manipulation, such as liquid separation and filtration.

In the second process, if the first step of reacting the cationic compound generating compound is carried out solely, in other words, if a second step is not carried out, it is same as the process of the tetrakis(fluoroaryl)borate derivative.ether complex. According to the above process, an inexpensive and highly-pure tetrakis(fluoroaryl)borate derivative.ether complex, which is useful as an intermediate for producing the tetrakis(fluoroaryl)borate derivative, can be produced efficiently.

In the second producing process, it is preferable to carry out the second step of removing the polyfunctional ether from the tetrakis(fluoroaryl)borate derivative.ether complex by heating the tetrakis(fluoroaryl)borate derivative.ether complex within a reaction vessel, so that the polyfunctional ether is distilled out from the reaction vessel.

The heating temperature is not especially limited as long as the polyfunctional ether can be removed from the tetrakis (fluoroaryl)borate derivative.ether complex. However, a preferable temperature is 40° C. or above, and a range between 40° C. and 200° C. is further preferable. A heating time is not especially limited, either.

To distill out the polyfunctional ether from the reaction vessel, the temperature inside the reaction vessel must be raised higher than the boiling point of the polyfunctional ether under the current pressure inside the reaction vessel. Thus, the pressure inside the reaction vessel may be reduced optionally. Consequently, the polyfunctional ether can be distilled out at a relatively low temperature.

Also, in the second step, the tetrakis(fluoroaryl)borate derivative.ether complex can be in the form of a solution dissolved into the solvent, or suspended in the solvent.

In case that the reaction is carried out using a solution of the tetrakis(fluoroaryl)borate derivative.ether complex, a solution in which tetrakis(fluoroaryl)borate is dissolved can be used as the solvent (either entirely or partially). Thus, the tetrakis(fluoroaryl)borate derivative can be produced using the solution of the tetrakis(fluoroaryl)borate derivative.ether complex obtained in the first step without isolating the ether complex from the solution.

In the second producing process, if the second step of removing the polyfunctional ether from the tetrakis (fluoroaryl)borate derivative.ether complex is carried out solely, in other words, if the first step is not carried out, the producing process is same as the producing process of an inexpensive and highly-pure tetrakis(fluoroaryl)borate derivative efficiently.

Other and further objects, features, and advantages of the present invention will appear more fully from the following description. Also; the benefits of the present invention will be apparent from the ensuing explanation.

THE BEST MODE FOR IMPLEMENTING THE INVENTION

The present invention will be explained in detail by way of examples; however, the present invention is not limited to the following disclosure. In the following examples, NMR (Nuclear Magnetic Resonance) spectrum data are measured using tetramethyl silane (TMS) as a reference reagent in case of $^1$H-NMR, and using trifluoro acetate as the reference reagent in case of $^{19}$F-NMR, by setting the signal of each reference reagent to 0 ppm.

EXAMPLE 1

Here, 100 ml of a mixed solution of diethyl ether and toluene containing 0.0257 mol of tetrakis (pentafluorophenyl)borate.magnesium bromide as tetrakis (fluoroaryl)borate.magnesium halide is charged to a reaction vessel equipped with a thermometer, a dropping funnel, a stirrer, and a reflux condenser. A mixing volume ratio of diethyl ether and toluene as the solvent is 1:1. The mixed solution contains 0.0771 mol of magnesium bromide fluoride as the impurities. Meanwhile, 100 ml (0.100 mol) of an aqueous solution of sodium carbonate serving as the carboxylate is charged to the dropping funnel.

Then, the aqueous solution is dropped to the mixed solution over 10 minutes at room temperature with stirring of the mixed solution, and the reaction solution is stirred for further 30 minutes at room temperature. In other words, the purifying process ① of the present invention is adopted herein. When the stirring ends, the deposit (magnesium carbonate) is removed by subjecting the reaction solution to suction filtration.

The filtrate is separated into an organic layer and a water layer, after which the water layer is extracted twice using 50 ml of ethyl acetate in each. Then, ethyl acetate (approximately 100 ml) used as the extraction liquid is added to the organic layer, while magnesium sulfate anhydride serving as a drying agent is added to dry the same.

When the organic layer is dried, diethyl ether, toluene, and ethyl acetate are distilled out from the organic layer under reduced pressure, whereby brown crystals of tetrakis (pentafluorophenyl)borate.sodium are obtained as the tetrakis(fluoroaryl)borate compound.

A survival rate of magnesium in the crystals is measured through X-ray fluorescence analysis, and no magnesium is detected in the crystals. Thus, it turned out that the crystals do not contain the impurities, such as magnesium halide.

Also, the yield of tetrakis(pentafluorophenyl) borate.sodium is found by measuring $^{19}$F-NMR. More specifically, $^{19}$F-NMR is measured under predetermined conditions using p-fluorotoluene as an internal standard reagent. Then, a peak integral of a fluorine atom of p-fluorotoluene, and a peak integral of fluorine atoms at the ortho-position of a pentafluorophenyl group in tetrakis (pentafluorophenyl)borate.sodium are computed from the resulting $^{19}$F-NMR chart first, and thence an amount of tetrakis(pentafluorophenyl)borate.sodium is computed using the above two peak integrals. The yield and purity of tetrakis(pentafluorophenyl)borate.sodium thus found are 89.1 mol % and 96.0%, respectively.

EXAMPLE 2

Here, 100 ml of a mixed solution of diethyl ether and toluene containing 0.025 mol of tetrakis (pentafluorophenyl) borate.magnesium bromide is charged to a reaction vessel of the same type as the one used in Example 1. A mixing volume ratio of diethyl ether and toluene is 1:1. Meanwhile, 100 ml (0.100 mol) of an aqueous solution of sodium acetate serving as the carboxylate is charged to the dropping funnel.

Then, the aqueous solution is dropped to the mixed solution over 10 minutes at room temperature with stirring of the mixed solution, and the reaction solution is stirred for further 60 minutes at room temperature. In other words, the purifying process ① of the present invention is adopted. When the stirring ends, the resulting solution is separated to an organic layer and a water layer, and the water later is extracted once using 50 ml of ethyl acetate. Subsequently, ethyl acetate serving as an extraction liquid is added to the organic layer, while magnesium sulfate anhydride is added to dry the same.

When the organic layer is dried, diethyl ether, toluene, and ethyl acetate are distilled out from the organic layer under reduced pressure, whereby brown crystals of tetrakis (pentafluorophenyl)borate.sodium are obtained. The yield and purity of tetrakis(pentafluorophenyl)borate.sodium found in the same manner as Example 1 are 92.1 mol % and 97.4%, respectively.

EXAMPLE 3

Here, 160 ml of a solution (concentration: 29.5 mol %) of di-n-butyl ether containing 0.047 mol of tetrakis (pentafluorophenyl)borate.magnesium bromide, and 300 ml (0.300 mol) of 1N-hydrochloric acid serving as the acid are charged to a separatory funnel having a capacity of 500 ml. Then, the separatory funnel is shaken satisfactorily first, and thence allowed to stand, whereby the solution is separated to an organic layer and a water layer. In other words, the purifying process ② of the present invention is adopted. The organic layer thus obtained is dried with an addition of magnesium sulfate anhydride.

When the organic layer is dried, di-n-butyl ether serving as the solvent is distilled out from the organic layer under reduced pressure, whereby a hydrogen compound of tetrakis (pentafluorophenyl)borate. is obtained. The yield of the hydrogen compound of tetrakis(pentafluorophenyl)borate. found in the same manner as Example 1 is 89.7 mol %.

EXAMPLE 4

Here, 47.9 g of a solution (concentration: 38.7 mol %) of toluene containing 0.018 mol of tetrakis(pentafluorophenyl)

borate.magnesium bromide, and 160 ml (0.160 mol) of 1N-hydrochloric acid are charged to a separatory funnel having a capacity of 300 ml. Then, the separatory funnel is shaken satisfactorily first, and thence allowed to stand, whereby the solution is separated to an organic layer and a water layer.

Then, the organic layer and 30 ml (0.030 mol) of an aqueous solution of 1N-sodium hydroxide serving as the hydroxide are charged to a conical flask equipped with a stirrer and having a capacity of 200 ml, and the reaction solution is stirred for one hour at room temperature. When the stirring ends, the solution is separated to an organic layer and a water layer. In other words, the purifying process ③ of the present invention is adopted. The organic layer thus obtained is dried with an addition of magnesium sulfate anhydride.

When the organic layer is dried, toluene is distilled out from the organic layer under reduced pressure, whereby crystals of tetrakis(pentafluorophenyl)borate.sodium are obtained. The yield of tetrakis(pentafluorophenyl)borate.sodium found in the same manner as Example 1 is 93.5 mol %.

EXAMPLE 5

Here, 45.6 g of a solution (concentration: 37.4 mol %) of toluene containing 0.017 mol of tetrakis(pentafluorophenyl)borate.magnesium bromide, and 75 ml (0.150 mol) of 0.5N-sulfuric acid serving as the acid are charged to a separatory funnel having a capacity of 300 ml. Then, the separatory funnel is shaken satisfactorily first, and thence allowed to stand, whereby the solution is separated to an organic layer and a water layer.

Then, the organic layer and 20 ml (0.020 mol) of an aqueous solution of 1N-sodium hydroxide are charged to a conical flask equipped with a stirrer and having a capacity of 200 ml, and the reaction solution is stirred for one hour at room temperature. When the stirring ends, the solution is separated to an organic layer and a water layer. In other words, the purifying process ③ of the present invention is adopted. The organic layer thus obtained is dried with an addition of magnesium sulfate anhydride.

When the organic layer is dried, toluene is distilled out from the organic layer under reduced pressure, whereby crystals of tetrakis(pentafluorophenyl)borate.sodium are obtained. The yield of tetrakis(pentafluorophenyl)borate.sodium found in the same manner as Example 1 is 91.5 mol %.

EXAMPLE 6

Here, 50 ml (0.100 mol) of an aqueous solution of oxalic acid serving as the acid is charged to a reaction vessel of the same type as the one used in Example 1. Meanwhile, 100 ml of a solution of di-n-butyl ether containing 0.025 mol of tetrakis(pentafluorophenyl)borate.magnesium bromide is charged to the dropping funnel.

Then, the solution is dropped to the aqueous solution over 10 minutes at room temperature with stirring of the aqueous solution, and the reaction solution is stirred for further 60 minutes at room temperature. When the stirring ends, the resulting solution is separated to an organic layer and a water layer, after which the organic layer is washed with a 10 wt % aqueous solution of sodium hydroxide serving as the alkali metal hydroxide. Then, the washed solution is separated to an organic layer and a water layer. In other words, the purifying process ③ of the present invention is adopted. The organic layer thus obtained is dried with an addition of magnesium sulfate anhydride.

When the organic layer is dried, di-n-butyl ether is distilled out from the organic layer under reduced pressure, whereby crystals of tetrakis(pentafluorophenyl)borate.sodium are obtained. The yield of tetrakis(pentafluorophenyl)borate.sodium found in the same manner as Example 1 is 95.0 mol %.

EXAMPLE 7

Here, 100 ml of a mixed solution of diethyl ether and di-n-butyl ether containing 0.042 mol of tetrakis(pentafluorophenyl)borate.magnesium bromide is charged to a reaction vessel of the same type as the one used in Example 1. A mixing volume ratio of diethyl ether and di-n-butyl ether as the solvent is 1:6. Meanwhile, 132 g of a 10 wt % aqueous solution of hydrochloric acid is charged to the dropping funnel.

Then, the aqueous solution is dropped to the mixed solution over 10 minutes at room temperature with stirring of the mixed solution, and the reaction solution is stirred for further 60 minutes at room temperature. When the stirring ends, the resulting solution is separated to an organic layer and a water layer. The organic layer thus obtained is washed with a 15 wt % aqueous solution of sodium succinate dibasic serving as the carboxylate, after which the solution is separated to an organic layer and a water layer. In other words, the purifying process ④ of the present invention is adopted. The organic layer thus obtained is dried with an addition of magnesium sulfate anhydride.

When the organic layer is dried, diethyl ether and di-n-butyl ether are distilled out from the organic layer under reduced pressure, whereby crystals of tetrakis(pentafluorophenyl)borate.sodium are obtained. The yield of tetrakis(pentafluorophenyl)borate.sodium found in the same manner as Example 1 is 97.9 mol %.

EXAMPLE 8

Here, 100 ml of a mixed solution of diethyl ether and di-n-butyl ether containing 0.041 mol of tetrakis(pentafluorophenyl)borate.magnesium bromide is charged to a reaction vessel of the same type as the one used in Example 1. A mixing volume ratio of diethyl ether and di-n-butyl ether is 1:6. Meanwhile, 132 g of a 10 wt % aqueous solution of hydrochloric acid is charged to the dropping funnel.

Then, the aqueous solution is dropped to the mixed solution over 10 minutes at room temperature with stirring of the mixed solution, and the reaction solution is stirred for 60 minutes at room temperature. When the stirring ends, the resulting solution is separated to an organic layer and a water layer. The organic layer thus obtained is washed with a 10 wt % aqueous solution of sodium carbonate, after which the solution is separated to an organic layer and a water layer. In other words, the purifying process ④ of the present invention is adopted. The organic layer thus obtained is dried with an addition of magnesium sulfate anhydride.

When the organic layer is dried, diethyl ether and di-n-butyl ether are distilled out from the organic layer under reduced pressure, whereby crystals of tetrakis(pentaflurorphenyl)borate.sodium are obtained. The yield of tetrakis(pentafluorophenyl)borate.sodium found in the same manner as Example 1 is 95.6 mol %.

EXAMPLE 9

Here, 16.1 g of tetrakis(pentafluorophenyl)borate.sodium obtained in Example 1 and 100 ml of ethyl acetate serving as the reaction solvent are charged to a reaction vessel of the same type as the one used in Example 1. Meanwhile, 100 ml (0.025 mol) of an aqueous solution of N,N-dimethylaniline.hydrochloride serving as the cation seed generating compound is charged to the dropping funnel.

Then, the aqueous solution is dropped to the solution over 10 minutes at room temperature with stirring of the solution, and the reaction solution is let undergo reaction for one hour at room temperature with stirring. When the reaction ends, the reaction solution is separated to an organic layer and a water layer, and the water layer is extracted once using 50 ml of ethyl acetate. Then, ethyl acetate serving as an extraction liquid is added to the organic layer, while magnesium sulfate anhydride is added to dry the same.

When the organic layer is dried, ethyl acetate is distilled out from the organic layer under reduced pressure, whereupon black crystals are obtained. The crystals are washed with 50 ml of diisopropyl ether, whereby light-brown N,N-dimethyl anilinium.tetrakis(pentafluorophenyl)borate is obtained as the tetrakis(fluoroaryl)borate derivative. The yield of N,N-dimethyl anilinium.tetrakis (pentafluorophenyl)borate found in the same manner as Example 1, that is, by measuring $^{19}$F-NMR using p-fluorotoluene as the internal standard reagent, is 89.9 mol %.

EXAMPLE 10

Here, 16.6 g of tetrakis(pentafluorophenyl)borate.sodium obtained in Example 2 and 100 ml of ethyl acetate are charged to a reaction vessel of the same type as the one used in Example 1. Meanwhile, 100 ml (0.025 mol) of an aqueous solution of N,N-dimethylaniline.hydrochloride is charged to the dropping funnel.

Then, the aqueous solution is dropped to the solution over 10 minutes at room temperature with stirring of the solution, and the reaction solution is let undergo reaction for one hour at room temperature with stirring. When the reaction ends, the reaction solution is separated to an organic layer and a water layer, and the water layer is extracted once using 50 ml of ethyl acetate. Then, ethyl acetate serving as an extraction liquid is added to the organic layer, while magnesium sulfate anhydride is added to dry the same.

When the organic layer is dried, ethyl acetate is distilled out from the organic layer under reduced pressure, whereupon brown crystals are obtained. The crystals are washed with 50 ml of diisopropyl ether, whereby light-gray N,N-dimethyl anilinium.tetrakis (pentafluorophenyl)borate is obtained. The yield of N,N-dimethyl anilinium.tetrakis (pentaflurophenyl)borate found in the same manner as Example 9 is 83.0 mol %.

EXAMPLE 11

Here, 59.8 g of a solution (concentration: 35.7 mol %) of di-n-butyl ether containing 0.021 mol of tetrakis (pentafluorophenyl)borate.magnesium bromide and 250 ml (0.250 mol) of 1N-formic acid serving as the acid are charged to a separatory funnel having a capacity of 500 ml. Then, the separatory funnel is shaken satisfactorily first, and thence allowed to stand, whereby the solution is separated to an organic layer and a water layer. After the water layer is taken out, 70 ml (0.014 mol) of an aqueous solution of 2N-lithium hydroxide serving as the hydroxide is added to the organic layer. Then, the separatory funnel is shaken satisfactorily again, and subsequently allowed to stand, whereby the solution is separated to an organic layer and a water layer. In other words, the purifying process ③ of the present invention is adopted. Then, magnesium sulfate anhydride is added to the organic layer to dry the same.

Subsequently, the organic layer is charged to a 4-neck flask equipped with a thermometer, a dropping funnel, a stirrer, and a reflux condenser, and having a capacity of 200 ml. Meanwhile, 2.84 g (0.023 mol) of N,N-dimethylaniline serving as the cation seed generating compound is charged to the dropping funnel.

Then, N,N-dimethylaniline is dropped to the organic layer over 15 minutes at room temperature with stirring of the organic layer, and the reaction solution is let undergo reaction for one hour at room temperature with stirring. When the reaction ends, di-n-butyl ether is distilled out from the organic layer under reduced pressure, whereby N,N-dimethyl anilinium.tetrakis (pentafluorophenyl)borate is obtained. The yield of N,N-dimethyl anilinium.tetrakis (pentafluorophenyl)borate found in the same manner as Example 9 is 91.2 mol %.

EXAMPLE 12

Here, 80 ml of a solution (concentration: 29.5 mol %) of di-n-butyl ether containing 0.023 mol of tetrakis (pentafluorophenyl)borate.magnesium bromide, and 150 ml (0.150 mol) of 1N-hydrochloric acid are charged to a separatory funnel having a capacity of 500 ml. Then, the separatory funnel is shaken satisfactorily first, and thence allowed to stand, whereby the solution is separated to an organic layer and a water layer. After the water layer is taken out, 33.0 ml (0.031 mol) of a 10 wt % aqueous solution of sodium carbonate is added to the organic layer. Then, the separatory funnel is shaken satisfactorily again, and subsequently allowed to stand, whereby the solution is separated to an organic layer and a water layer. In other words, the purifying process ④ of the present invention is adopted. Then, magnesium sulfate anhydride is added to the organic layer to dry the same.

Then, the organic layer and 3.72 g (0.024 mol) of N,N-dimethylaniline.hydrochloride are charged to a 4-neck flask equipped with a thermometer, a stirrer, and a reflux condenser and having a capacity of 200 ml. Then, the organic layer is let undergo reaction for one hour at room temperature with stirring. When the reaction ends, di-n-butyl ether is distilled out from the organic layer under reduced pressure, whereby N,N-dimethyl anilinium.tetrakis (pentafluorophenyl)borate is obtained. The yield of N,N-dimethyl anilinium.tetrakis(pentafluorophenyl)borate found in the same manner as Example 9 is 86.7 mol %.

EXAMPLE 13

The reaction and manipulation are carried out in the same manner as Example 12 except that 83.0 ml (0.031 mol) of a 20 wt % aqueous solution of sodium succinate dibasic is charged instead of 33.0 ml of the 10 wt % aqueous solution of sodium carbonate; and that an amount of used N,N-dimethylaniline.hydrochloride is increased to 3.99 g (0.025 mol) from 3.72 g (0.024 mol), whereby N,N-dimethyl anilinium.tetrakis(pentafluorophenyl)borate is obtained. The yield of N,N-dimethyl anilinium.tetrakis (pentafluorophenyl)borate found in the same manner as Example 9 is 87.3 mol %.

EXAMPLE 14

Here, 50.0 g of a solution of di-n-butyl ether containing 0.016 mol of tetrakis(pentafluorophenyl)borate.magnesium bromide, and 140 ml of 1N-hydrochloride are charged to a separatory funnel having a capacity of 500 ml. Then, the separatory funnel is shaken satisfactorily first, and thence allowed to stand, whereby the solution is separated to an organic layer and a water layer. In other words, the purifying process ② of the present invention is adopted. Then, magnesium sulfate anhydride is added to the organic layer to dry the same.

Subsequently, the organic layer is charged to a 4-neck flask equipped with a thermometer, a dropping funnel, a stirrer, and a reflux condenser and having a capacity of 200 ml. Meanwhile, 2.06 g (0.017 mol) of N,N-dimethylaniline is charged to the dropping funnel.

Then, N,N-dimethylaniline is dropped to the organic layer over 10 minutes at room temperature with stirring of the organic layer, and the reaction solution is let undergo reaction for one hour at room temperature with stirring. When the reaction ends, di-n-butyl ether is distilled out from the organic layer under reduced pressure, whereby N,N-dimethyl anilinium.tetrakis (pentafluorophenyl)borate is obtained. The yield of N,N-dimethyl anilinium.tetrakis (pentafluorophenyl)borate found in the same manner as Example 9 is 94.8 mol %.

EXAMPLE 15

Here, 130.6 g of a solution (concentration: 15.8 mol %) of di-n-butyl ether containing 0.021 mol of tetrakis (pentafluorophenyl)borate.magnesium bromide and 180 ml (0.180 mol) of 1N-sulfuric acid serving as the acid are charged to a separatory funnel having a capacity of 500 ml. Then, the separatory funnel is shaken satisfactorily first, and thence allowed to stand, whereby the solution is separated to an organic layer and a water layer. In other words, the purifying process ② of the present invention is adopted. Then, magnesium sulfate anhydride is added to the organic layer to dry the same.

Subsequently, the organic layer is charged to a 4-neck flask equipped with a thermometer, a dropping funnel, a stirrer, and a reflux condenser and having a capacity of 200 ml. Meanwhile, 2.74 g (0.027 mol) of N,N-dimethylaniline is charged to the dropping funnel.

Then, N,N-dimethylaniline is dropped to the organic layer over 15 minutes at room temperature with stirring of the organic layer, and the reaction solution is let undergo reaction for one hour at room temperature with stirring. When the reaction ends, di-n-butyl ether is distilled out from the organic layer under reduced pressure, whereby N,N-dimethyl anilinium.tetrakis (pentafluorophenyl)borate is obtained. The yield of N,N-dimethyl anilinium.tetrakis (pentafluorophenyl)borate found in the same manner as Example 9 is 90.3 mol %.

EXAMPLE 16

Here, 120.7 g of a solution (concentration: 16.6 mol %) of di-n-butyl ether containing 0.020 mol of tetrakis (pentafluorophenyl)borate.magnesium bromide and 90 ml (0.180 mol) of 2N-formic acid are charged to a separatory funnel having a capacity of 500 ml. Then, the separatory funnel is shaken satisfactorily first, and thence allowed to stand, whereby the solution is separated to an organic layer and a water layer. In other words, the purifying process ② of the present invention is adopted. Then, magnesium sulfate anhydride is added to the organic layer to dry the same.

Subsequently, the organic layer is charged to a 4-neck flask equipped with a thermometer, a dropping funnel, a stirrer, and a reflux condenser and having a capacity of 200 ml. Meanwhile, 2.62 g (0.022 mol) of N,N-dimethylaniline is charged to the dropping funnel.

Then, N,N-dimethylaniline is dropped to the organic layer over 15 minutes at room temperature with stirring of the organic layer, and the reaction solution is let undergo reaction for one hour at room temperature with stirring. When the reaction ends, di-n-butyl ether is distilled out from the organic layer under reduced pressure, whereby N,N-dimethyl anilinium.tetrakis(pentafluorophenyl)borate is obtained. The yield of N,N-dimethyl anilinium.tetrakis (pentafluorophenyl)borate found in the same manner as Example 9 is 89.6 mol %.

EXAMPLE 17

Here, 200 ml of a solution of di-n-butyl ether containing 0.045 mol of tetrakis(pentafluorophenyl)borate.lithium serving as tetrakis(fluoroaryl)borate is charged to a reaction vessel equipped with a thermometer, a dropping funnel, a reflux condenser, and a stirrer. Meanwhile, 0.45 mol of 1,2-dimethoxy ethane serving as the polyfunctional ether is charged to the dropping funnel.

Then, 1,2-dimethoxy ethane in the dropping funnel is dropped to the content in the reaction vessel over 10 minutes at room temperature with stirring of the content, and the reaction solution is stirred for further 30 minutes at the same temperature (room temperature), whereby the reaction solution is crystallized. The resulting crystals are collected by subjecting the content in the reaction vessel to the suction filtration, and then washed with 20 ml of isopropyl ether.

The crystals thus obtained are dried under reduced pressure, whereby white crystals of a tetrakis (pentafluorophenyl)borate.lithium.1,2-dimethoxy ethane complex is obtained as the tetrakis(fluoroaryl) borate.polyfunctional ether complex.

The yield of the tetrakis(pentafluorophenyl) borate.lithium.1,2-dimethoxy ethane complex is found by measuring $^{19}$F-NMR (Nuclear Magnetic Resonance) spectrum. In other words, $^{19}$F-NMR is measured under predetermined conditions using p-fluorotoluene as the internal standard reagent. Then, a ratio of a peak integral of a fluorine atom of p-fluorotoluene, and a peak integral of fluorine atoms at the ortho-position of a pentafluorophenyl group in the tetrakis(pentafluorophenyl)borate.lithium. 1,2-dimethoxy ethane complex is computed from the resulting $^{19}$F-NMR chart first, and thence a weight of the tetrakis (pentafluorophenyl)borate.lithium.1,2-dimethoxy ethane complex is computed using the above peak integral ratio.

The yield of the tetrakis(pentafluorophenyl) borate.lithium.1,2-dimethoxy ethane complex with respect to tetrakis(pentafluorophenyl)borate.lithium thus found is 85.2 mol %, and the purity of the tetrakis (pentafluorophenyl)borate.lithium.1,2-dimethoxy ethane complex thus found is 99%.

Further, $^1$H-NMR is measured under predetermined conditions using p-fluorotoluene as the internal standard reagent. Then, a ratio of a peak integral of a methyl group of p-fluorotoluene, and a peak integral of methyl groups of 1,2-dimethoxy ethane is computed from the resulting $^1$H-NMR chart first, and thence a mol amount of 1,2-dimethoxy ethane is computed using the above peak integral ratio.

A mole ratio of tetrakis(pentafluorophenyl)borate.lithium and 1,2-dimethoxy ethane in the tetrakis(pentafluorophenyl) borate.lithium.1,2-dimethoxy ethane complex thus found is 1:2.

The tetrakis(pentafluorophenyl)borate.lithium.1,2-dimethoxy ethane complex is identified through the analysis of the measured melting point, IR (Infrared absorption spectrum), $^{19}$F-NMR, and $^1$H-NRM, as well as the elemental analysis. Here, given the following as the data obtained through the analysis,

| | |
|---|---|
| melting point: | 119° C.–120° C. |
| IR (KBr, cm$^{-1}$): | 2947, 1642, 1515, 1464, 1279, 1121, 1083, 978, 868 |
| $^{19}$F-NMR (CDCl$_3$, δ): | −56.9, −87.1, −91.1 |
| $^1$H-NRM (CDCl$_3$, δ): | 3.41 (6H, s), 3.57 (4H, s) | elemental analysis: $C_{24}F_{20}BLi \cdot 2C_4H_{10}O_2$ then, a computed value (%) is, hydrogen: 2.33, carbon: 44.37, fluorine: 43.87 and an analysis value (%) is, hydrogen: 2.47, carbon: 44.36, fluorine: 43.33.

EXAMPLE 18

Here, a mixed solution is prepared by dissolving 0.0214 mol of tetrakis(pentafluorophenyl)borate.sodium serving as tetrakis(fluoroaryl)borate into a mixed solvent of diethyl ether and di-n-butyl ether (volume ratio of diethyl ether and di-n-butyl ether: 1:1), and 100 ml of which is charged to a reaction vessel of the same type as the one used in Example 17. Meanwhile, 0.900 mol of 1,2-dimethoxy, ethane is charged to the dropping funnel.

Then, 1,2-dimethoxy ethane in the dropping funnel is dropped to the content in the reaction vessel over 10 minutes at room temperature with stirring of the content, and the reaction solution is stirred for further 30 minutes at the same temperature (room temperature). Then, diethyl ether and excessive 1,2-dimethoxy ethane are distilled out from the reaction vessel under reduced pressure, whereby the reaction solution is crystallized. The crystals are collected by subjecting the content in the reaction vessel to the suction filtration, and then washed with 100 ml of n-hexane.

Then, the washed crystals are dried under reduced pressure, whereby white-yellow crystals of a tetrakis (pentafluorophenyl)borate.sodium.1,2-dimethoxy ethane complex are obtained as the tetrakis(fluoroaryl)borate polyfunctional ether complex.

The yield of the tetrakis(pentafluorophenyl)borate.sodium.1,2-dimethoxy ethane complex with respect to the tetrakis(fluoroaryl)borate.sodium and the purity of the tetrakis(pentafluorophenyl)borate.sodium.1,2-dimethoxy ethane complex analyzed in the same manner as Example 17 are 95.7 mol % and 99%, respectively.

Also, a mole ratio of tetrakis(pentafluorophenyl)borate.sodium and 1,2-dimethoxy ethane in the tetrakis (pentafluorophenyl)borate.sodium.1,2-dimethoxy ethane complex is 1:3.

The tetrakis(pentafluorophenyl)borate.sodium.1,2-dimethoxy ethane complex is identified with the following analysis data. That is, given

| | |
|---|---|
| melting point: | 159° C.–162° C. |
| IR (KBr, cm$^{-1}$): | 2948, 2908, 1645, 1471, 1278, 1128, 1087, 975, 860 |
| $^{19}$F-NMR (CDCl$_3$, δ): | −57.4, −86.8, −91.2 |
| $^1$H-NRM (CDCl$_3$, δ): | 3.35 (6H, s), 3.53 (4H, s) | elemental analysis: $C_{24}F_{20}BNa \cdot 3C_4H_{10}O_2$ then, a computed value (%) is, hydrogen: 3.06, carbon: 43.73, fluorine: 38.43 and an analysis value (%) is, hydrogen: 3.03, carbon: 45.13, fluorine: 38.86.

EXAMPLE 19

Here, 200 ml of a solution of di-n-butyl ether containing 0.0414 mol of tetrakis(pentafluorophenyl)borate.potassium serving as tetrakis(fluoroaryl)borate is charged to a reaction vessel of the same type as the one used in Example 17. Meanwhile, 0.900 mol of 1,2-dimethoxy ethane is charged to the dropping funnel.

Then, 1,2-dimethoxy ethane in the dropping funnel is dropped to the content in the reaction vessel over 10 minutes at room temperature with stirring of the content, and the reaction solution is stirred for further 30 minutes at the same temperature (room temperature). Then, the reaction solution is heated to 110° C. to distill out excessive 1,2-dimethoxy ethane and subsequently cooled to room temperature, whereby the reaction solution is crystallized. The crystals are collected by subjecting the content in the reaction vessel to the suction filtration, and then washed with 100 ml of n-hexane. Then, the washed crystals are dried under reduced pressure, whereby white-yellow powders of a tetrakis (pentafluorophenyl)borate.potassium.1,2-dimethoxy ethane complex are obtained as the tetrakis (fluoroaryl) borate.polyfunctional ether complex.

The yield and purity of the tetrakis (pentafluorophenyl)borate.potassium 1,2-dimethoxy ethane complex analyzed in the same manner as Example 17 are 71.5 mol % and 99%, respectively. Also, a mole ratio of tetrakis (pentafluorophenyl)borate.potassium and 1,2-dimethoxy ethane in the tetrakis(pentafluorophenyl)borate.potassium.1, 2-dimethoxy ethane complex is 1:3.

The tetrakis(pentafluorophenyl)borate.potassium.1,2-dimethoxy ethane complex is identified with the following analysis data. That is, given

| | |
|---|---|
| melting point: | 127° C.–130° C. |
| IR (KBr, cm$^{-1}$): | 2944, 2906, 1645, 1515, 1466, 1277, 1125, 1087, 978, 857 |
| $^{19}$F-NMR (CDCl$_3$, δ): | −57.2, −86.7, −90.9 |
| $^1$H-NRM (CDCl$_3$, δ): | 3.33 (6H, s), 3.51 (4H, s) | elemental analysis: $C_{24}F_{20}BK \cdot 3\ C_4H_{10}O_2$ then, a computed value (%) is, hydrogen: 3.08, carbon: 44.44, fluorine: 39.09 and an analysis value (%) is, hydrogen: 3.07, carbon: 44.03, fluorine: 37.98.

EXAMPLE 20

Here, 0.0214 mol of tetrakis(pentafluorophenyl)borate.lithium is suspended in 50 ml of ion-exchange water in a reaction vessel of the same type as the one used in Example 17, and the resulting suspended liquid is heated to 50° C., so that tetrakis(pentafluorophenyl)borate.lithium is dissolved into the ion-exchange water. Then, 50 ml of 1,2-diethoxy ethane serving as the polyfunctional ether is added to the resulting solution, and the reaction solution is stirred for 10 minutes, whereby the reaction mixed solution is separated to an organic layer and a water layer. The water layer is extracted using 50 ml of 1,2-diethoxy ethane and the organic layer thus obtained is mixed with another organic layer which has been separated before.

The mixed organic layer is dried with magnesium sulfate anhydride, and subsequently, the solvent (1,2-diethoxy ethane) is distilled out under reduced pressure, whereby brown crystals of a tetrakis(pentafluorophenyl)borate.lithium.1,2-diethoxy ethane complex are obtained as the tetrakis(fluoroaryl)borate.polyfunctional ether complex.

The yield and purity of the tetrakis(pentafluorophenyl)borate.lithium.1,2-diethoxy ethane complex analyzed in the same manner as Example 17 are 91.1 mol % and 99%, respectively. Also, a mole ratio of tetrakis(pentafluorophenyl)borate.lithium and 1,2-diethoxy ethane in the tetrakis(pentafluorophenyl)borate.lithium.1,2-diethoxy ethane complex is 1:3.

The tetrakis(pentafluorophenyl)borate.lithium.1,2-dimethoxy ethane complex is identified with the following analysis data,

| | |
|---|---|
| melting point: | 170° C.–172° C. |
| IR (KBr, cm$^{-1}$): | 2986, 2941, 1645, 1516, 1465, 1276, 1119, 1084, 1066, 980 |
| $^{19}$F-NMR (DMSO-d$_6$, δ): | −56.8, −87.3, −91.1 |
| $^1$H-NRM (DMSO-d$_6$, δ): | 1.24 (6H, t, J = 7.2 Hz), 3.66 (4H, q, J = 7.2 Hz), 3.69 (4H, s). |

EXAMPLE 21

Here, 0.010 mol of tetrakis(pentafluorophenyl)borate.sodium is suspended in 50 ml of ion-exchange water in a reaction vessel of the same type as the one used in Example 17, and 50 ml of 1,2-diethoxy ethane is added to the resulting suspended liquid. Then, the reaction mixed solution is stirred for 10 minutes, whereby the reaction solution is separated to an organic layer and a water layer. The water layer is extracted using 50 ml of 1,2-diethoxy ethane and the organic layer thus obtained is mixed with another organic layer which has been separated before.

The mixed organic layer is dried with magnesium sulfate anhydride, and the solvent is distilled out under reduced pressure, whereby light-brown crystals of a tetrakis(pentafluorophenyl)borate.sodium.1,2-diethoxy ethane complex are obtained as the tetrakis(fluoroaryl)borate.polyfunctional ether complex.

The yield and purity of the tetrakis(pentafluorophenyl)borate.sodium.1,2-diethoxy ethane complex analyzed in the same manner as Example 17 are 94.2 mol % and 99%, respectively. Also, a mole ratio of tetrakis(pentafluorophenyl)borate.sodium and 1,2-diethoxy ethane in the tetrakis(pentafluorophenyl)borate.sodium.1,2-diethoxy ethane complex is 1:3.

The tetrakis(pentafluorophenyl)borate.sodium.1,2-dimethoxy ethane complex is identified with the following analysis data,

| | |
|---|---|
| melting point: | 167° C.–169° C. |
| IR (KBr, cm$^{-1}$): | 2986, 2940, 1645, 1516, 1465, 1275, 1119, 1085, 1066, 980 |
| $^{19}$F-NMR (DMSO-d$_6$, δ): | −55.5, −84.6, −89.3 |
| $^1$H-NRM (DMSO-d$_6$, δ): | 1.13 (6H, t, J = 7.2 Hz), 3.45 (4H, q, J = 7.2 Hz), 3.49 (4H, s). |

EXAMPLE 22

Here, 20 ml of a solution of di-n-butyl ether containing 0.004 mol of tetrakis(pentafluorophenyl)borate.potassium is charged to a reaction vessel of the same type as the one used in Example 17. Then, 0.020 mol of 1,2-diethoxy ethane is added to the above solution, and the reaction solution is stirred for 10 hours at room temperature, whereby the reaction solution is crystallized. The crystals are collected by subjecting the content in the reaction vessel to the suction filtration, and then washed with 10 ml of di-n-butyl ether.

Then, the washed crystals are dried under reduced pressure, whereby white crystals of a tetrakis(pentafluorophenyl)borate.potassium.1,2-diethoxy ethane complex are obtained as the tetrakis(fluoroaryl)borate.polyfunctional ether complex.

The yield and purity of the tetrakis(pentafluorophenyl)borate.potassium.1,2-diethoxy ethane complex analyzed in the same manner as Example 17 are 70.7 mol % and 99.9%, respectively. Also, a mole ratio of tetrakis(pentafluorophenyl)borate.potassium and 1,2-diethoxy ethane in the tetrakis(pentafluorophenyl)borate.potassium.1,2-diethoxy ethane complex is 1:3.

The tetrakis(pentafluorophenyl)borate.potassium.1,2-dimethoxy ethane complex is identified with the following analysis data,

| | |
|---|---|
| melting point: | 113° C.–114° C. |
| IR (KBr, cm$^{-1}$): | 2983, 2935, 1645, 1515, 1464, 1276, 1085, 978 |
| $^{19}$F-NMR (DMSO-d$_6$, δ): | −56.6, −85.6, −90.1 |
| $^1$H-NRM (DMSO-d$_6$, δ): | 1.11 (6H, t, J = 7.2 Hz), 3.44 (4H, q, J = 7.2 Hz), 3.45 (4H, s). |

EXAMPLE 23

Here, 20 ml of a solution of di-n-butyl ether containing 0.004 mol of tetrakis(pentafluorophenyl)borate.lithium is charged to a reaction vessel of the same type as the one used in Example 17. Then, 0.016 mol of diethylene glycol dimethyl ether serving as the polyfunctional ether is added to the above solution, and the reaction solution is stirred for 10 hours at room temperature, whereby the reaction solution is crystallized. The crystals are collected by subjecting the content in the reaction vessel to the suction filtration, and then washed with 10 ml of di-n-butyl ether.

Then, the washed crystals are dried under reduced pressure, whereby white crystals of a tetrakis(pentafluorophenyl)borate.lithium.diethylene glycol dimethyl ether complex are obtained as the tetrakis(fluoroaryl)borate.polyfunctional ether complex.

The yield and purity of the tetrakis(pentafluorophenyl)borate.lithium.diethylene glycol dimethyl ether complex analyzed in the same manner as Example 17 are 85.0 mol % and 99%, respectively. Also, a mole ratio of tetrakis(pentafluorophenyl)borate.lithium and diethylene glycol dimethyl ether in the tetrakis(pentafluorophenyl)borate.lithium.diethylene glycol dimethyl ether complex is 1:2.5.

The tetrakis(pentafluorophenyl)borate.lithium.diethylene glycol dimethyl ether complex is identified with the following analysis data,

| | |
|---|---|
| melting point: | 193° C.–195° C. |
| IR (KBr, cm$^{-1}$): | 2940, 1644, 1515, 1464, 1279, 1114, 1084, 979 |

-continued

| | |
|---|---|
| $^{19}$F-NMR (CDCl$_3$, δ): | −56.7, −87.3, −91.1 |
| $^1$H-NRM (CDCl$_3$, δ): | 3.36 (6H, s) |
| | 3.54–3.56 (4H, m) |
| | 3.63–3.65 (4H, m). |

EXAMPLE 24

Here, 20 ml of a solution of di-n-butyl ether containing 0.005 mol of tetrakis(pentafluorophenyl)borate.sodium is charged to a reaction vessel of the same type as the one used in Example 17. Then, 0.016 mol of diethylene glycol dimethyl ether is added to the above solution, and the reaction solution is stirred for 10 hours at room temperature, whereby the reaction solution is crystallized. The crystals are collected by subjecting the content in the reaction vessel to the suction filtration, and then washed with 10 ml of di-n-butyl ether.

Then, the washed crystals are dried under reduced pressure, whereby white crystals of a tetrakis (pentafluorophenyl)borate.sodium.diethylene glycol dimethyl ether complex are obtained as the tetrakis(fluoroaryl)borate.polyfunctional ether complex.

The yield and purity of the tetrakis(pentafluorophenyl)borate.sodium.diethylene glycol dimethyl ether complex analyzed in the same manner as Example 17 are 85.4 mol % and 99%, respectively. Also, a mole ratio of tetrakis (pentafluorophenyl)borate.sodium and diethylene glycol dimethyl ether in the tetrakis (pentafluorophenyl)borate.sodium.diethylene glycol dimethyl ether complex is 1:3.

The tetrakis(pentafluorophenyl)borate.sodium.diethylene glycol dimethyl ether complex is identified with the following analysis data,

| | |
|---|---|
| melting point: | 167° C.–169° C. |
| IR (KBr, cm$^{-1}$): | 2941, 1644, 1514, 1461, 1276, 1113, 1085, 977 |
| $^{19}$F-NMR (CDCl$_3$, δ): | −56.4, −87.3, −91.3 |
| $^1$H-NRM (CDCl$_3$, δ): | 3.38 (6H, s) |
| | 3.38–3.57 (4H, m) |
| | 3.59–3.61 (4H, m). |

EXAMPLE 25

Here, 20 ml of a solution of di-n-butyl ether containing 0.005 mol of tetrakis(pentafluorophenyl)borate.potassium is charged to a reaction vessel of the same type as the one used in Example 17. Then, 0.016 mol of diethylene glycol dimethyl ether is added to the above solution, and the reaction solution is stirred for 10 hours at room temperature, whereby the reaction solution is crystallized. The crystals are collected by subjecting the content in the reaction vessel to the suction filtration, and then washed with 10 ml of di-n-butyl ether.

Then, the washed crystals are dried under reduced pressure, whereby white crystals of a tetrakis (pentafluorophenyl)borate.potassium.diethylene glycol dimethyl ether complex are obtained as the tetrakis(fluoroaryl)borate.polyfunctional ether complex.

The yield and purity of the tetrakis(pentafluorophenyl)borate.potassium.diethylene glycol dimethyl ether complex analyzed in the same manner as Example 17 are 98.5 mol % and 99%, respectively. Also, a mole ratio of tetrakis (pentafluorophenyl)borate.potassium and diethylene glycol dimethyl ether in the tetrakis(pentafluorophenyl) borate.potassium.diethylene glycol dimethyl ether complex is 1:3.

The tetrakis(pentafluorophenyl)borate.potassium.diethylene glycol dimethyl ether complex is identified with the following analysis data,

| | |
|---|---|
| melting point: | 96° C.–97° C. |
| IR (KBr, cm$^{-1}$): | 2940, 2906, 1645, 1514, 1465, 1276, 1110, 1087, 980 |
| $^{19}$F-NMR (CDCl$_3$, δ): | −56.9, −87.1, −91.1 |
| $^1$H-NRM (CDCl$_3$, δ): | 3.33 (6H, s) |
| | 3.51–3.53 (4H, m) |
| | 3.55–3.58 (4H, m). |

EXAMPLE 26

Here, a mixed solution is prepared by dissolving 0.259 mol of tetrakis(pentafluorophenyl)borate.magnesium bromide serving as tetrakis(fluoroaryl)borate and 0.0194 mol of magnesium bromide fluoride into a mixed solvent of diethyl ether and di-n-butyl ether (a volume ratio of diethyl ether and di-n-butyl ether: 1:1), and 100 ml of which is charged to a reaction vessel of the same type as the one used in Example 17. Meanwhile, 0.0550 mol of 1,2-dimethoxy ethane is charged to the dropping funnel.

Then, 1,2-dimethoxy ethane in the dropping funnel is dropped to the content in the reaction vessel over 15 minutes at room temperature with stirring of the content, and the content in the reaction vessel is heated to 140° C. with stirring, so that diethyl ether and excessive 1,2-dimethoxy ethane are distilled out. After the reaction mixture is cooled to room temperature and crystallized, the crystals are collected by subjecting the reaction mixture to the suction filtration, and then washed with 100 ml of di-n-butyl ether.

The washed crystals are dried under reduced pressure, whereby light-yellow powders of a tetrakis (pentafluorophenyl)borate.magnesium bromide.1,2-dimethoxy ethane complex are obtained as the tetrakis (fluoroaryl)borate.polyfunctional ether complex.

The yield and purity of the tetrakis (pentafluorophenyl)borate.magnesium bromide-1,2-dimethoxy ethane complex analyzed in the same manner as Example 17 are 94.5 mol % and 99%, respectively. The tetrakis(pentafluorophenyl)borate.magnesium bromide-1,2-dimethoxy ethane complex is analyzed through the X-ray fluorescence analysis, and no magnesium is detected, meaning that magnesium bromide fluoride is completely removed. The data obtained by the analysis are:

| | |
|---|---|
| melting point: | 230° C. or above |
| IR (KBr, cm$^{-1}$): | 2953, 1631, 1516, 1465, 1112, 1087, 980 |
| $^{19}$F-NMR (CDCl$_3$, δ): | −56.6, −87.6, −90.1 |
| $^1$H-NRM (CDCl$_3$, δ): | 3.26 (6H, s) |
| | 3.44 (4H, s). |

EXAMPLE 27

Here, 100 ml of a solution of di-n-butyl ether containing 0.040 mol of a hydrogen compound of tetrakis (pentafluorophenyl)borate.hydride is charged to a reaction vessel of the same type as the one used in Example 17. Meanwhile, 0.140 mol of 1,2-dimethoxy ethane is charged to the dripping funnel.

Then, 1,2-dimethoxy ethane in the dropping funnel is dropped to the content in the reaction vessel over 15 minutes at room temperature with stirring of the content, and the reaction solution is stirred for further one hour at the same temperature (room temperature). When the stirring ends, the content in the reaction vessel is heated under reduced pressure, so that di-n-butyl ether and excessive 1,2-dimethoxy ethane are distilled out.

Subsequently, the content is cooled to room temperature, whereby light-brown oil of a tetrakis(pentafluorophenyl)borate.1,2-dimethoxy ethane complex is obtained.

The yield and purity of the tetrakis(pentafluorophenyl)borate.1,2-dimethoxy ethane complex analyzed in the same manner as Example 17 are 90.0 mol % and 98%, respectively. The data obtained by the analysis are,

| $^{19}$F-NMR (CDCl$_3$, δ): | −56.8, −87.4, −91.3 |
|---|---|
| $^{1}$H-NRM (CDCl$_3$, δ): | 3.39 (6H, s) |
| | 3.60 (4H, s) |
| | 9.83 (1H, br). |

EXAMPLE 28

Here, 108 g of a solution of di-n-butyl ether containing 32.43 wt % (0.050 mol) of tetrakis(pentafluorophenyl)borate.sodium is charged to a reaction vessel of the same type as the one used in Example 17. Meanwhile, 0.100 mol of 1,2-dimethoxy ethane is charged to the dropping funnel.

Then, 1,2-dimethoxy ethane in the dropping funnel is dropped to the content in the reaction vessel over 10 minutes at 20° C. while the content in the reaction vessel is stirred at room temperature, and the reaction solution is stirred for further 10 hours at the same temperature (room temperature), whereby the reaction solution is crystallized. The crystals are collected by subjecting the content in the reaction vessel to the suction filtration, and then washed with 18 g of di-n-butyl ether.

The washed crystals are dried under reduced pressure, whereby light-yellow crystals of a tetrakis(pentafluorophenyl)borate.sodium.1,2-dimethoxy ethane complex are obtained.

The yield and purity of the tetrakis(pentafluorophenyl)borate.sodium.1,2-dimethoxy ethane complex analyzed in the same manner as Example 17 are 70.0 mol % and 99%, respectively.

EXAMPLE 29

Here, 108 g of a solution of di-n-butyl ether containing 32.43 wt % (0.050 mol) of tetrakis(pentafluorophenyl)borate.sodium is charged to a reaction vessel of the same type as the one used in Example 17. Meanwhile, 0.150 mol of 1,2-dimethoxy ethane is charged to the dropping funnel. Then, 1,2-dimethoxy ethane in the dropping funnel is dropped to the content in the reaction vessel over 10 minutes at 20° C. while the content is stirred at room temperature, and the reaction solution is stirred for further 10 hours at the same temperature (room temperature), whereby the reaction solution is crystallized.

The crystals are collected by subjecting the content in the reaction vessel to the suction filtration, and then washed with 18 g of di-n-butyl ether. The washed crystals are dried under reduced pressure, whereby white crystals of a tetrakis(pentafluorophenyl)borate.sodium.1,2-dimethoxy ethane complex are obtained.

The yield and purity of the tetrakis(pentafluorophenyl)borate.sodium.1,2-dimethoxy ethane complex analyzed in the same manner as Example 17 are 85.8 mol % and 99%, respectively.

EXAMPLE 30

Here, 90 g of a solution of di-n-butyl ether containing 22.0 wt % (0.028 mol) of tetrakis(pentafluorophenyl)borate.sodium is charged to a reaction vessel of the same type as the one used in Example 17. Meanwhile, 0.098 mol of 1,2-dimethoxy ethane is charged to the dropping funnel. Then, 1,2-dimethoxy ethane in the dropping funnel is dropped to the content in the reaction vessel over 10 minutes at 20° C. while the content is stirred at room temperature, and the reaction solution is stirred for further 10 hours at the same temperature (room temperature), whereby the reaction solution is crystallized.

The crystals are collected by subjecting the content in the reaction vessel to the suction filtration, and then washed with 10 g of di-n-butyl ether. The washed crystals are dried under reduced pressure, whereby white crystals of a tetrakis(pentafluorophenyl)borate.sodium.1,2-dimethoxy ethane complex are obtained.

The yield and purity of the tetrakis(pentafluorophenyl)borate.sodium.1,2-dimethoxy ethane complex analyzed in the same manner as Example 17 are 95.3 mol % and 99%, respectively.

EXAMPLE 31

Here, 0.0152 mol of tetrakis(pentafluorophenyl)borate.potassium.1,2-dimethoxy ethane complex serving as the tetrakis(fluoroaryl)borate.ether complex and 100 ml of a mixed solvent of acetone and ion-exchange water (mixing volume ratio: 1:1) are charged to a reaction vessel equipped with a thermometer, a dropping funnel, a distillation device, and a stirrer. Meanwhile, 20 ml of an aqueous solution of N,N-dimethylaniline.hydrochloride (an amount of N,N-dimethylaniline.hydrochloride is 0.0167 mol) serving as the cation seed generating compound is charged to the dropping funnel.

Then, the content in the reaction vessel is heated at 90° C. for 30 minutes with stirring, so that 1,2-dimethoxy ethane and acetone are distilled out from the reaction series through the distillation device, whereby an aqueous solution of tetrakis(pentafluorophenyl)borate.potassium is obtained as tetrakis(fluoroaryl)borate.

Subsequently, the aqueous solution of N,N-dimethylaniline.hydrochloride in the dropping funnel is dropped to the content in the reaction vessel over 10 minutes at the same temperature (90° C.), and the resulting mixed solution is stirred for further 30 minutes at the same temperature (90° C.). Then, after the reaction solution is cooled to room temperature and crystallized, the content in the reaction vessel is subjected to the suction filtration, and the resulting cake is washed with ion-exchange water.

Then, the washed cake is dried under reduced pressure, whereby white powders of N,N-dimethyl anilinium.tetrakis(pentafluorophenyl)borate is obtained as the tetrakis(fluoroaryl)borate derivative.

The yield of the N,N-dimethyl anilinium.tetrakis(pentafluorophenyl)borate thus obtained is found by measuring $^{19}$F-NMR (Nuclear, Magnetic Resonance) spectrum. In other words, $^{19}$F-NMR is measured under predetermined conditions using p-fluorotoluene as the internal standard reagent. Then, a ratio of a peak integral of a fluorine atom of p-fluorotoluene, and a peak integral of fluorine atoms at the ortho-position of a pentafluorophenyl group in N,N-dimethyl anilinium.tetrakis(pentafluorophenyl)borate is computed from the resulting $^{19}$F-NMR chart first, and thence a weight of N,N-dimethyl anilinium.tetrakis (pentafluorophenyl)borate is computed using the above peak integral ratio.

The yield of N,N-dimethyl anilinium.tetrakis (pentafluorophenyl)borate based on the tetrakis (pentafluorophenyl)borate.potassium.1,2-dimethoxy ethane complex thus found is 92.5 mol % and the purity of N,N-dimethyl anilinium.tetrakis(pentafluorophenyl)borate is 99%.

EXAMPLE 32

Here, 0.0446 mol of the tetrakis(pentafluorophenyl) borate.potassium.1,2-dimethoxy ethane complex and 200 g of ion-exchange water are charged to a reaction vessel of the same type as the one used in Example 31, and the content is stirred, whereby a suspended liquid is obtained.

Subsequently, the suspended,liquid is heated with stirring, so that 1,2-dimethoxy ethane is distilled out through the distillation device, after which the content is cooled to 50° C. As a consequence, an aqueous solution of tetrakis (pentafluorophenyl)borate.potassium is obtained as tetrakis (fluoroaryl)borate.

Then, 80 ml of an aqueous solution of N,N-dimethylaniline sulfate (an amount of N,N-dimethyl aniline sulfate is 0.060 mol) serving as the cation seed generating compound is charged to the dropping funnel. Then, the aqueous solution of N,N-dimethylaniline sulfate is dropped to the aqueous solution of tetrakis(pentafluorophenyl) borate.potassium at 50° C. with stirring. Then, after the reaction solution is cooled to room temperature and crystallized, the content in the reaction vessel is subjected to the suction filtration, after which the resulting cake is washed with ion-exchange water.

Further, the washed cake is dried under reduced pressure, whereby white powders of N,N-dimethyl anilinium.tetrakis (pentafluorophenyl)borate are obtained. The yield and purity of N,N-dimethyl anilinium.tetrakis(pentafluorophenyl) borate analyzed in the same manner as Example 31 are 90.9 mol % and 99%, respectively.

EXAMPLE 33

Here, 2.29 mmol of the tetrakis(pentafluorophenyl) borate.sodium.1,2-dimethoxy ethane complex serving as the tetrakis(fluoroaryl)borate.ether complex and 40 ml of di-n-butyl ether are charged to a reaction vessel of the same type as the one used in Example 31. The content is stirred and a mixed solution is obtained. Meanwhile, 10 ml of an aqueous solution of N,N-dimethylaniline.hydrochloride (an amount of N,N-dimethylaniline.hydrochloride is 3.51 mmol) is charged to the dropping funnel.

Then, the aqueous solution of N,N-dimethylaniline.hydrochloride in the dropping funnel is dropped to the mixed solution at room temperature with stirring of the mixed solution. When the dropping ends, the mixed liquid in the reaction vessel is heated, so that 1,2-dimethoxy ethane is distilled out through the distillation device.

Subsequently, the reaction solution is cooled to room temperature and separated to a di-n-butyl ether layer and a water layer. The di-n-butyl ether layer is distilled out from the di-n-butyl ether layer under reduced pressure, whereby the di-n-butyl ether layer is crystallized. The crystals are collected by subjecting the content in the reaction vessel to the suction filtration, and then washed with a slight amount of di-n-butyl ether.

The washed crystals are dried overnight at 80° C. under reduced pressure, whereby white powders of N,N-dimethyl anilinium.tetrakis(pentafluorophenyl)borate are obtained. The yield and purity of N,N-dimethyl anilinium.tetrakis (pentafluorophenyl)borate analyzed in the same manner as Example 31 are 58.8 mol % and 99%, respectively.

EXAMPLE 34

Here, a solution is prepared by dissolving 0.123 mol of the tetrakis(pentafluorophenyl)borate.lithium.1,2-diethoxy ethane complex serving as the tetrakis (fluoroaryl) borate.ether complex into a mixed solvent of acetone and ion-exchange water (mixing volume ratio: 1:1), and 300 ml of which is charged to a reaction vessel equipped with a thermometer, a dropping funnel, a reflux condensing pipe, and a stirrer. Meanwhile, 100 ml of an aqueous solution of N,N-dimethylaniline-hydrochloride (an amount of N,N-dimethylaniline-hydrochloride is 0.135 mol) is charged to the dropping funnel.

Then, the aqueous solution of N,N-dimethylaniline.hydrochloride in the dropping funnel is dropped to the content in the reaction vessel over 30 minutes at room temperature with stirring of the content, and the reaction solution is stirred for further 30 minutes at the same temperature (room temperature), whereby the reaction solution is crystallized. The content in the reaction vessel is subjected to the suction filtration, and the resulting cake is washed with ion-exchange water.

The washed cake is dried under reduced pressure, whereby white powders of an N,N-dimethyl anilinium.tetrakis(pentafluorophenyl)borate.1,2-diethoxy ethane complex are obtained as the tetrakis(fluoroaryl) borate derivative-ether complex.

The yield and purity of the N,N-dimethyl anilinium.tetrakis(pentafluorophenyl)borate.1,2-diethoxy ethane complex analyzed in the same manner as Example 31 are 49.8 mol % and 99%, respectively.

Further, $^{1}$H-NMR is measured under predetermined conditions using p-fluorotoluene as the internal standard reagent. Then, a ratio of a peak integral of a methyl group of p-fluorotoluene, a peak integral of methyl groups of N,N-dimethylaniline, and a peak integral of a methyl group of 1,2-diethoxy ethane is computed from the resulting $^{1}$H-NMR chart first, and thence weights of N,N-dimethylaniline and 1,2-diethoxy ethane are computed using the above peak integral ratio. A mole ratio of N,N-dimethyl anilinium tetrakis(pentafluorophenyl)borate and 1,2-diethoxy ethane in the N,N-dimethyl anilinium.tetrakis (pentafluorophenyl)borate.1,2-diethoxy ethane complex found based on the weights of N,N-dimethylaniline and 1,2-diethoxy ethane is 1:1.

Meanwhile, the filtrate obtained by the above filtration is concentrated under reduced pressure, whereby white crystals of the N,N-dimethyl anilinium.tetrakis (pentafluorophenyl)borate.1,2-diethoxy ethane complex are collected. The yield of the collected complex is 45.0 mol % (thereby making a total yield of 94.8 mol %).

The N,N-dimethyl anilinium.tetrakis(pentafluorophenyl) borate.1,2-diethoxy ethane complex is identified through the analysis of the measured melting point, IR (Infrared absorption spectrum), $^{19}$F-NMR, and $^1$H-NRM. The data obtained through the analysis are,

| | |
|---|---|
| melting point: | 162° C.–163° C. |
| IR (KBr, cm$^{-1}$): | 2984, 2941, 1644, 1515, 1465, 1277, 1112, 1069, 980 |
| $^{19}$F-NMR (CDCl$_3$, δ): | −56.8, −87.1, −91.0 |
| $^1$H-NRM (CDCl$_3$, δ): | 1.22 (6H, t, J = 7.2 Hz), |
| | 3.22 (6H, s), |
| | 3.40–3.68 (8H, m), |
| | 7.31–7.33 (2H, m), |
| | 7.56–7.59 (3H, m). |

EXAMPLE 35

Here, 0.0188 mol of the tetrakis(pentaflurophenyl)borate.potassium.1,2-dimethoxy ethane complex is charged to a reaction vessel of the same type as the one used in Example 34, and suspended in 50 ml of ion-exchange water. Meanwhile, 20 ml of an Aqueous solution of N,N-dimethylaniline.hydrochloride (an amount of N,N-dimethylaniline.hydrochloride is 0.0207 mol) is charged to the dropping funnel.

Then, the aqueous solution of N,N-dimethylaniline.hydrochloride in the dropping funnel is dropped to the suspended liquid over 30 minutes at room temperature with stirring of the suspended liquid, and the reaction solution is stirred for further 30 minutes at the same temperature (room temperature), whereby the reaction solution is crystallized. The content in the reaction vessel is subjected to the suction filtration and the resulting cake is washed with ion-exchange water.

The washed cake is dried under reduced pressure, whereby white powders of an N,N-dimethyl anilinium.tetrakis(pentafluorophenyl)borate.1,2-dimethoxy ethane complex are obtained as the tetrakis(fluoroaryl)borate derivative.ether complex.

The yield and purity of the N,N-dimethyl anilinium.tetrakis(pentafluorophenyl)borate.1,2-dimethoxy ethane complex analyzed in the same manner as Example 31 are 93.1 mol % and 99%, respectively.

Further, a mole ratio of N,N-dimethyl anilinium.tetrakis(pentafluorophenyl)borate and 1,2-dimethoxy ethane in the N,N-dimethyl anilinium.tetrakis(pentafluorophenyl)borate.1,2-dimethoxy ethane complex found in the same manner as Example 34 is 1:1.

The N,N-dimethyl anilinium.tetrakis(pentafluorophenyl)borate.1,2-dimethoxy ethane complex is identified with the following analysis data,

| | |
|---|---|
| melting point: | 129° C.–131° C. |
| IR (KBr, cm$^{-1}$): | 2952, 2908, 1646, 1517, 1456, 1277, 1083, 978 |
| $^{19}$F-NMR (CDCl$_3$, δ): | −56.6, −85.5, −90.1 |
| $^1$H-NRM (CDCl$_3$, δ): | 3.11 (6H, s) |
| | 3.25 (6H, s), |
| | 3.42 (4H, s), |
| | 7.20–7.50 (5H, m). |

EXAMPLE 36

Here, 6.44 mmol of the tetrakis(pentafluorophenyl)borate.lithium.1,2-dimethoxy ethane complex is charged to a reaction vessel of the same type as the one used in Example 34, to which 20 ml of acetone and 20 ml of ion-exchange water are added to dissolve the complex. Meanwhile, 20 ml of an aqueous solution of N,N-dimethylaniline.hydrochloride (an amount of N,N-dimethylaniline.hydrochloride is 7.08 mmol) is charged to the dropping funnel.

Then, the aqueous solution of N,N-dimethylaniline.hydrochloride is dropped to the content in the reaction vessel over 10 minutes at room temperature with stirring of the content, and the reaction solution is stirred for further one hour at the same temperature (room temperature). Subsequently, the content in the reaction vessel is heated to 40° C. under reduced pressure, so that acetone is distilled out, after which the content is extracted using isopropyl ether. The extraction liquid is dried with magnesium sulfate anhydride. Then, magnesium sulfate anhydride is filtered out and isopropyl ether is distilled out under reduced pressure, whereby light-yellow oil of an N,N-dimethyl anilinium.tetrakis(pentafluorophenyl)borate.1,2-dimethoxy ethane complex is obtained.

The yield and purity of the N,N-dimethyl anilinium.tetrakis(pentafluorophenyl)borate.1,2-dimethoxy ethane complex analyzed in the same manner as Example 31 are 82.8 mol % and 99%, respectively.

EXAMPLE 37

Here, 1.03 mmol of the tetrakis(pentafluorophenyl)borate.sodium.diethylene glycol dimethyl ether complex is charged to a reaction vessel of the same type as the one used in Example 34, to which 10 ml of ion-exchange water is added to suspend the complex. Meanwhile, 10 ml of an aqueous solution of N,N-dimethylaniline.hydrochloride (an amount of N,N-dimethylaniline.hydrochloride is 1.23 mmol) is charged to the dropping funnel.

Then, the aqueous solution of N,N-dimethylaniline.hydrochloride is dropped to the content in the reaction vessel over 10 minutes at room temperature with stirring of the content, and the reaction solution is stirred for further one hour at room temperature, whereby the reaction solution is crystallized. The content in the reaction vessel is subjected to the suction filtration, and the resulting cake is washed with ion-exchange water.

Then, the washed cake is dried under reduced pressure, whereby white powders of an N,N-dimethyl anilinium.tetrakis(pentafluorophenyl)borate.diethylene glycol dimethyl ether complex are obtained as the tetrakis(fluoroaryl)borate derivative.ether complex.

The yield and purity of the N,N-dimethyl anilinium.tetrakis(pentafluorophenyl)borate.diethylene glycol dimethyl ether complex analyzed in the same manner as Example 31 are 89.3 mol % and 99%, respectively.

Further, a mole ratio of N,N-dimethyl anilinium.tetrakis(pentafluorophenyl)borate and diethylene glycol dimethyl ether in the N,N-dimethyl anilinium.tetrakis(pentafluorophenyl)borate.diethylene glycol dimethyl ether complex found in the same manner as Example 34 is 1:1.

The N,N-dimethyl anilinium.tetrakis(pentafluorophenyl)borate.diethylene glycol dimethyl ether complex is identified with the following analysis data,

| | |
|---|---|
| melting point: | 179° C.–180° C. |
| IR (KBr, cm$^{-1}$): | 2940, 2904, 1644, 1515, 1468, 1462, 1278, 1114, 1084, 978 |
| $^{19}$F-NMR (CDCl$_3$, δ): | −56.8, −87.1, −91.0 |
| $^1$H-NRM (CDCl$_3$, δ): | 3.25 (6H, s), |
| | 3.38 (6H, s), |
| | 3.41–3.58 (4H, m), |
| | 3.59–3.66 (4H, m), |
| | 7.34–7.36 (2H, m), |
| | 7.57–7.58 (3H, m). |

EXAMPLE 38

Here, a solution of acetone is prepared by dissolving 6.44 mmol of the tetrakis(pentafluorophenyl)borate.lithium.1,2-dimethoxy ethane complex is dissolved into acetone, and 30 ml of which is charged to a reaction vessel of the same type as the one used in Example 31.

The content in the reaction vessel is heated for 30 minutes with stirring, so that 1,2-dimethoxy ethane and acetone are distilled out; from the reaction series through the distillation device. Further, a temperature inside the reaction vessel is heated to 100° C. and subsequently cooled to room temperature.

Consequently, light-yellow oil of tetrakis (pentafluorophenyl)borate.lithium is obtained as tetrakis (fluoroaryl)borate. The yield of tetrakis(pentafluorophenyl) borate.lithium analyzed in the same manner as Example 31 is 95.3 mol %.

EXAMPLE 39

Here, a solution is prepared by dissolving 5.34 mmol of N,N-dimethyl anilinium.tetrakis(pentafluorophenyl) borate.1,2-dimethoxy ethane complex obtained in Example 35 into a mixed solvent of acetone and ion-exchange water (mixing volume ratio: 1:1), and 40 ml of which is charged to a reaction vessel of the same type as the one used in Example 31.

A temperature inside the reaction vessel is raised to 80° C. while the content in the reaction vessel is stirred. Then, after the temperature (80° C.) is maintained for 30 minutes, a pressure inside the reaction vessel is reduced at the same temperature (80° C.), so that 1,2-dimethoxy ethane, acetone, and ion exchange water are distilled out from the reaction series.

Consequently, white powders of N,N-dimethyl anilinium.tetrakis(pentaflurorphenyl)borate are obtained. The yield and purity of N,N-dimethyl anilinium.tetrakis (pentaflurorphenyl)borate analyzed in the same manner as Example 31 are 93.6 mol % and 99%, respectively.

EXAMPLE 40

Here, a solution is prepared by dissolving 1.24 mmol of the tetrakis(pentafluorophenyl)borate.lithium.1,2-dimethoxy ethane complex into a mixed solvent of acetone and ion-exchange water (mixing volume ratio: 1:1), and 20 ml of which is charged to a reaction vessel of the same type as the one used in Example 31. Meanwhile, 10 ml of an aqueous solution of N,N-dimethylaniline.hydrochloride (an amount of N,N-dimethylaniline.hydrochloride is 1.34 mmol) is charged to the dropping funnel.

Then, the aqueous solution of N,N-dimethylaniline.hydrochloride is dropped to the content in the reaction vessel over 10 minutes at room temperature with stirring of the content, and the reaction solution is stirred for further one hour at the same temperature (room temperature). Then, a temperature inside the reaction vessel is raised to 100° C. and the temperature (100° C.) is maintained for 30 minutes, so that acetone and 1,2-dimethoxy ethane are distilled out. After the reaction product is extracted using 20 ml of isopropyl ether, the extraction liquid is dried with magnesium sulfate anhydride. Then, after magnesium sulfate anhydride is filtered out, isopropyl ether is distilled out under reduced pressure.

Consequently, light-brown crystals of N,N-dimethyl anilinium.tetrakis(pentafluorophenyl)borate are obtained. The yield and purity of N,N-dimethyl anilinium.tetrakis (pentafluorophenyl)borate analyzed in the same manner as Example 31 are 95.6 mol % and 99%, respectively.

EXAMPLE 41

Here, a solution is prepared by dissolving 0.0152 mol of tetrakis(pentafluorophenyl)borate.potassium.1,2-dimethoxy ethane complex into a mixed solvent of acetone and ion-exchange water (mixing volume ratio: 1:1), and 100 ml of which is charged to a reaction vessel of the same type as the one used in Example 31. Meanwhile, 20 ml of an aqueous solution of N,N-dimethylaniline.hydrochloride (an amount of N,N-dimethylaniline.hydrochloride is 0.0167 mol) is charged to the dropping funnel.

Then, a temperature inside the reaction vessel is raised to 90° C. while the content in the reaction vessel is stirred, and the content is stirred for further 90 minutes at the same temperature (90° C.), so that acetone and 1,2-dimethoxy ethane are distilled out.

Then, the aqueous solution of N,N-dimethylaniline.hydrochloride is dropped to the content over 30 minutes at the same temperature (90° C.), after which a temperature inside the reaction vessel is cooled to room temperature to crystallize the reaction solution. The crystals are collected by subjecting the content in the reaction vessel to the suction filtration, and then washed with 100 ml of ion-exchange water.

The washed crystals are dried at 90° C. under reduced pressure, whereby light-yellow crystals of N,N-dimethyl anilinium.tetrakis(pentafluorophenyl)borate are obtained. The yield and purity of N,N-dimethyl anilinium.tetrakis (pentafluorophenyl)borate analyzed in the same manner as Example 31 are 94.0 mol % and 99%, respectively.

EXAMPLE 42

Here, 0.0103 mol of the tetrakis(pentafluorophenyl) borate.sodium.1,2-dimethoxy ethane complex and 50 ml of ion-exchange water are charged to a reaction vessel of the same type as the one used in, Example 31. Then, the content is stirred, whereby a suspended liquid is obtained.

Subsequently, the suspended liquid is heated with stirring, so that 1,2-dimethoxy ethane is distilled out through the distillation device, whereby an aqueous solution of tetrakis (pentafluorophenyl)borate.sodium is obtained as tetrakis (fluoroaryl)borate.

After the aqueous solution is cooled to 55° C., the distillation device of the reaction vessel is switched to the reflux condenser, while 0.0103 mol of tetraphenyl phosphonium bromide serving as the cation seed generating compound and 60 ml of acetone are added to the aqueous solution with stirring, whereby a suspended liquid is obtained.

The suspended liquid is heated with stirring, and refluxed over 1.5 hour. Further, the reflux condenser of the reaction vessel is switched to the distillation device at the reflux temperature. Consequently, 35.4 g of the solvent is distilled out. After the temperature inside the reaction vessel is cooled to room temperature and the reaction solution is crystallized, the content in the reaction vessel is subjected to the suction filtration, and the resulting cake is washed with ion-exchange water.

Then, the washed cake is dried at 80° C. under reduced pressure, whereby white crystals of tetraphenyl phosphonium.tetrakis(pentafluorophenyl)borate are obtained. The yield and purity of tetraphenyl phosphonium.tetrakis(pentafluorophenyl)borate analyzed in the same manner as Example 31 are 96.3 mol % and 99%, respectively.

EXAMPLE 43

Here, 0.015 mol of the tetrakis(pentafluorophenyl) borate.sodium.1,2-dimethoxy ethane complex and 50 ml of ion-exchange water are charged to a reaction vessel of the same type as the one used in Example 31. Then, the content is stirred, whereby a suspended liquid is obtained.

Subsequently, the suspended liquid is heated with stirring, so that 1,2-dimethoxy ethane is distilled out through the distillation device, whereby an aqueous solution of tetrakis (pentaflurorphenyl)borate.sodium is obtained.

After the aqueous solution is cooled to room temperature, another aqueous solution containing 0.016 mol of quinoline.hydrochloride serving as the cation seed generating compound is added to the cooled aqueous solution, and the resulting mixed aqueous solution is stirred for one hour. Then, the content in the reaction vessel is subjected to the suction filtration, and the resulting cake is washed with ion-exchange water.

Then, the washed cake is dried at 80° C. under reduced pressure, whereby white crystals of quinolinium.tetrakis (pentafluorophenyl)borate are obtained. The yield and purity of quinolinium.tetrakis (pentafluorophenyl)borate analyzed in the same manner as Example 31 are 82.3 mol % and 99%, respectively.

EXAMPLE 44

The reaction and manipulation are carried out in the same manner as Example 43 except that the used aqueous solution contains 0.016 mol of N-methyl pyridine iodide as the cation seed generating compound instead of quinoline.hydrochloride. Consequently, white crystals of N-methyl pyridinium.tetrakis(pentaflurorphenyl)borate are obtained. The yield and purity of N-methyl pyridinium.tetrakis (pentaflurorphenyl)borate analyzed in the same manner as Example 31 are 54.7 mol % and 99%, respectively.

EXAMPLE 45

The reaction and manipulation are carried out in the same manner as Example 43 except that the aqueous used instead of the aqueous solution of quinoline.hydrochloride contains 0.016 mol of trimethyl sulfonium iodide as the cation seed generating compound. Consequently, white crystals of trimethyl sulfonium.tetrakis(pentaflurorphenyl)borate are obtained. The yield and purity of trim ethyl sulfonium tetrakis(pentafluorophenyl)borate analyzed in the same manner as Example 31 are 89.5 mol % and 99%, respectively.

EXAMPLE 46

Here, 0.017 mol of tetrakis(pentafluorophenyl) borate.sodium.1,2-dimethoxy ethane complex and 50 ml of ion-exchange water are charged to a reaction vessel of the same type as the one used in Example 31. Then, the content is stirred, whereby a suspended liquid is obtained.

Subsequently, the suspended liquid is heated with stirring, so that 1,2-dimethoxy ethane is distilled out through the distillation device, whereby an aqueous solution of tetrakis (pentafluorophenyl)borate.sodium is obtained.

After the aqueous solution is cooled to room temperature, 0.016 mol of diphenyl iodonium chloride serving as the cation seed generating compound is added to the aqueous solution, and the reaction solution is stirred for three hours. Then, the content in the reaction vessel is subjected to the suction filtration, and the resulting cake is washed with ion-exchange water.

The washed cake is dried at 80° C. under reduced pressure, whereby white crystals of diphenyl iodonium.tetrakis(pentafluorophenyl)borate are obtained. The yield and purity of diphenyl iodonium.tetrakis (pentafluorophenyl)borate analyzed in the same manner as Example 31 are 92.3 mol % and 99%, respectively.

EXAMPLE 47

An aqueous solution of tetrakis(pentafluorophenyl) borate.sodium is obtained by carrying out the manipulation in the same manner as Example 46. The aqueous solution is solidified at 100° C. under reduced pressure, whereby 11.9 g of solid tetrakis(pentafluorophenyl)borate.sodium is obtained.

Then, the solid is suspended in 200 ml of n-hexane, and 0.019 mol of trityl chloride serving as the cation seed generating compound is added to the suspended liquid, after which the suspended liquid is stirred for six hours at the reflux temperature. After the suspended liquid is cooled to room temperature, the content in the reaction vessel is subjected to the suction filtration, and the resulting cake is dissolved into dichloromethane.

Then, an insoluble component (deposit) contained in the cake is removed through the suction filtration, and the resulting filtrate is concentrated under reduced pressure. Then, n-hexane is added to the concentrate until it is crystallized. After the crystals are allowed to stand for 16 hours, the content in the reaction vessel is subjected to the suction filtration, and the resulting cake is washed with n-hexane.

Then, the washed cake is dried at 80° C. under reduced pressure, whereby yellow crystals of trityl.tetrakis (pentafluorophenyl)borate are obtained. The yield and purity of trityl.tetrakis(pentafluorophenyl)borate analyzed in the same manner as Example 31 are 30.6 mol % and 99%, respectively.

Example embodiment and examples disclosed in THE BEST MODE FOR IMPLEMENTING THE INVENTION clause are provided to make the art, of the present invention apparent. Thus, the present invention shall not be construed limitedly to these examples and can be modified in many ways within the spirit of the present invention and the scope of the claims set forth below.

POSSIBLE INDUSTRIAL APPLICATION

The tetrakis(fluoroaryl)borate.ether complex and tetrakis (fluoroaryl)borate derivative obtained by the producing processes of the present invention are useful as, for example: a co-catalyst of the metallocene catalyst (polymeric catalyst) used in the cationic complex polymerization reaction; a photopolymeric catalyst for silicone; a cationic polymerization initiator used for the polymerization of a functional polymer or monomer through photochemical activation or irradiation of electronic beams; an intermediate for producing tetrakis(pentafluorophenyl)borate derivatives of various kinds; etc.

What is claimed is:

1. A tetrakis(fluoroaryl)borate.ether complex of Formula (4):

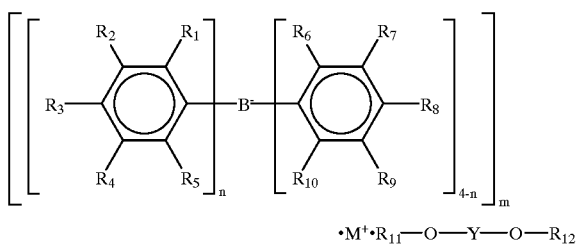

(4)

where each of $R_1$–$R_{10}$ represents a hydrogen atom, a fluorine atom, a hydrocarbon group, or an alkoxy group, provided that at least one of $R_1$–$R_5$ represents a fluorine atom and at least one of $R_6$–$R_{10}$ represents a fluorine atom, each of $R_{11}$ and $R_{12}$ represents a hydrocarbon group which may include a substituent group containing a hetero atom, Y represents a bivalent hydrocarbon group, M represents a hydrogen atom, an alkali metal, an alkaline earth metal, or alkaline earth metal halide, n represents 2 or 3, and m represents 1 when M represents a hydrogen atom, alkali metal, or alkaline earth metal halide, and 2 when M represents an alkaline earth metal.

2. A process for producing a tetrakis(fluoroaryl)borate.ether complex of Formula (4):

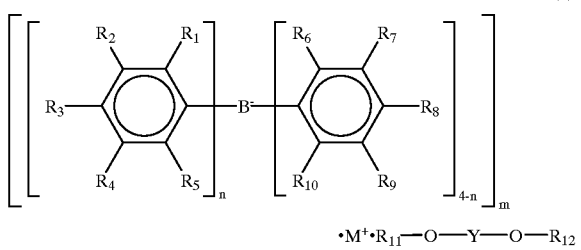

(4)

where each of $R_1$–$R_{10}$ represents a hydrogen atom, a fluorine atom, a hydrocarbon group, or an alkoxy group, provided that at least one of $R_1$–$R_5$ represents a fluorine atom and at least one of $R_6$–$R_{10}$ represents a fluorine atom, each of $R_{11}$ and $R_{12}$ represents a hydrocarbon group which may include a substituent group containing a hetero atom, Y represents a bivalent hydrocarbon group, M represents a hydrogen atom, an alkali metal, an alkaline earth metal, or an alkaline earth metal halide, n represents 2 or 3, and m represents 1 when M represents a hydrogen atom, an alkali metal, or an alkaline earth metal halide, and 2 when M represents an alkaline earth metal, comprising:

reacting tetrakis(fluoroaryl)borate of Formula (5):

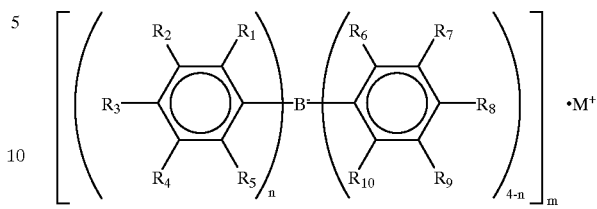

(5)

where each of $R_1$–$R_{10}$ represents a hydrogen atom, a fluorine atom, a hydrocarbon group, or an alkoxy group, provided that at least one of $R_1$–$R_5$ represents a fluorine atom and at least one of $R_6$–$R_{10}$ represents a fluorine atom, M represents a hydrogen atom, an alkali metal, an alkaline earth metal, or an alkaline earth metal halide, n represents 2 or 3, and m represents 1 when M represents a hydrogen atom, an alkali metal, or an alkaline earth metal halide, and 2 when M represents an alkaline earth metal, with an ether compound of Formula (6):

(6)

where each of $R_{11}$ and $R_{12}$ represents a hydrocarbon group which may include a substituent group containing a hetero atom, and Y represents a bivalent hydrocarbon group.

3. The process for producing a tetrakis(fluoroaryl) borate.ether complex of claim 2, wherein said tetrakis (fluoroaryl)borate is a hydrogen compound of tetrakis (pentafluorophenyl)borate, tetrakis(pentafluorophenyl) borate.magnesium bromide, tetrakis(pentafluorophenyl) borate.lithium, tetrakis(pentafluorophenyl)borate.sodium, or tetrakis(pentafluorophenyl)borate.potassium.

4. The process for producing a tetrakis(fluoroaryl) borate.ether complex of claim 2, wherein said ether compound is selected from the group consisting of ethylene glycol dialkyl ether, ethylene glycol dicyclo alkyl ether, diethylene glycol dialkyl ether, triethylene glycol dialkyl ether, and ethylene glycol diaryl ether and mixtures thereof.

5. A process for producing a tetrakis(fluoroaryl)borate derivative of Formula (2):

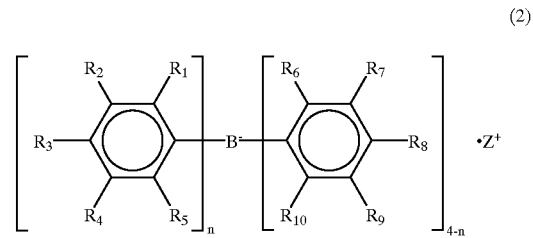

(2)

where each of $R_1$–$R_{10}$ represents a hydrogen atom, a fluorine atom, a hydrocarbon group, or an alkoxy group, provided that at least one of $R_1$–$R_5$ represents a fluorine atom and at least one of $R_6$–$R_{10}$ represents a fluorine atom, $Z^+$ represents a monovalent cationic compound, and n represents 2 or 3, comprising using, as a starting material, a tetrakis(fluoroaryl) borate.ether complex of Formula (4):

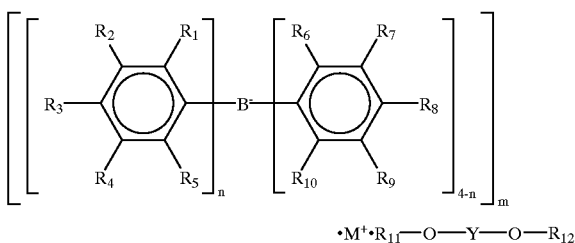

(4)

where each of $R_1$–$R_{10}$ represents a hydrogen atom, a fluorine atom, a hydrocarbon group, or an alkoxy group, provided that at least one of $R_1$–$R_5$ represents a fluorine atom and at least one of $R_6$–$R_{10}$ represents a fluorine atom, each of $R_{11}$ and $R_{12}$ represents a hydrocarbon group which may include a substituent group containing a hetero atom, Y represents a bivalent hydrocarbon group, M represents a hydrogen atom, an alkali metal, an alkaline earth metal, or an alkaline earth metal halide, n represents 2 or 3, and m represents 1 when M represents a hydrogen atom, an alkali metal, or an alkaline earth metal halide, and 2 when M represents an alkaline earth metal, and a compound generating monovalent cationic compounds.

6. The process for producing a tetrakis(fluoroaryl)borate derivative of claim 5, wherein said monovalent cationic compounds are selected from the group consisting of ammonium cations, anilinium cations, pyridinium cations, quinolinium cations, phosphonium cations, sulfonium cations, iodonium cations, carbenium cations and mixtures thereof.

7. The process for producing a tetrakis(fluoroaryl)borate derivative of claim 5, wherein said compound generating the monovalent cationic compounds is selected from the group consisting of a quaternary ammonium compound, a nitrogen-containing aromatic heterocyclic compound, a quaternary phosphonium compound, a sulfonium compound, an iodonium compound, a carbenium compound and mixtures thereof.

8. The process for producing a tetrakis(fluoroaryl)borate derivative of claim 5, wherein said compound generating the monovalent cationic compounds is selected from the group consisting of tri-n-butylamine.hydrochloride, N,N-dimethylaniline.hydrochloride, N,N-dimethylaniline.sulfate, quinoline.hydrochloride, N-methyl pyridine.iodide, tetraphenyl phosphonium bromide, trimethyl sulfonium iodide, diphenyl iodonium chloride, trityl chloride, and mixtures thereof.

9. The process for producing a tetrakis(fluoroaryl)borate derivative of claim 5, wherein said process includes the step of removing an ether compound of Formula (6):

$$R_{11}\text{—}O\text{—}Y\text{—}O\text{—}R_{12} \quad (6)$$

where each of $R_{11}$ and $R_{12}$ represents a hydrocarbon group which may include a substituent group containing a hetero atom, and Y represents a bivalent hydrocarbon group, from said reaction.

10. The process for producing a tetrakis(fluoroaryl)borate derivative of claim 9, wherein said ether compound is selected from the group consisting of ethylene glycol dialkyl ether, ethylene glycol dicyclo alkyl ether, diethylene glycol dialkyl ether, triethylene glycol dialkyl ether, ethylene glycol diaryl ether and mixtures thereof.

11. The process for producing a tetrakis(fluoroaryl)borate derivative of claim 9, wherein, after obtaining tetrakis(fluoroaryl)borate of Formula (5):

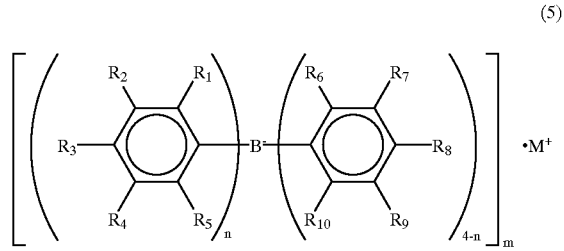

(5)

where each of $R_1$–$R_{10}$ represents a hydrogen atom, a fluorine atom, a hydrocarbon group, or an alkoxy group, provided that at least one of $R_1$–$R_5$ represents a fluorine atom and at least one of $R_6$–$R_{10}$ represents a fluorine atom, M represents a hydrogen atom, an alkali metal, an alkaline earth metal, or an alkaline earth metal halide, n represents 2 or 3, and m represents 1 when M represents a hydrogen atom, an alkali metal, or an alkaline earth metal halide, and 2 when M represents an alkaline earth metal, by removing said ether compound from said tetrakis(fluoroaryl)borate.ether complex, said tetrakis(fluoroaryl)borate is reacted with said compound generating the monovalent cationic compounds.

12. The process for producing a tetrakis(fluoroaryl)borate derivative of claim 9, wherein, after obtaining a tetrakis(fluoroaryl)borate derivative.ether complex of Formula (7):

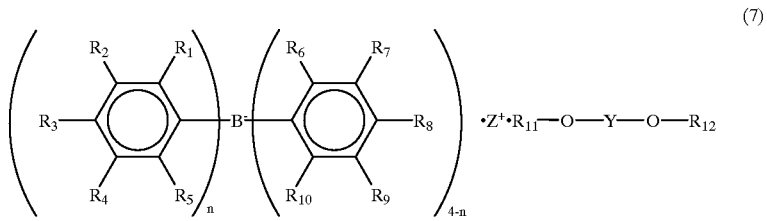

(7)

where each of $R_1$–$R_{10}$ represents a hydrogen atom, a fluorine atom, a hydrocarbon group, or an alkoxy group, provided that at least one of $R_1$–$R_5$ represents a fluorine atom and at least one of $R_6$–$R_{10}$ represents a fluorine atom, each of $R_{11}$ and $R_{12}$ represents a hydrocarbon group which may include a substituent group containing a hetero atom, Y represents a bivalent hydrocarbon group, $Z^+$ represents a monovalent cationic compound, and n represents 2 or 3, by reacting said tetrakis(fluoroaryl)borate.ether complex with said compound generating the monovalent cationic compound, said ether compound is removed from said tetrakis(fluoroaryl)borate derivative.ether complex.

* * * * *